US006855502B2

(12) United States Patent
Weigel et al.

(10) Patent No.: US 6,855,502 B2
(45) Date of Patent: *Feb. 15, 2005

(54) HYALURONATE SYNTHASE GENE AND USES THEREOF

(76) Inventors: Paul H. Weigel, 1109 Hidden Oaks, League City, TX (US) 77573; Paul L. DeAngelis, 2001 Ave. L #2, Galveston, TX (US) 77550; John Papaconstantinou, 43 Lebrun Ct. E., Galveston, TX (US) 77550

(*) Notice: Subject to any disclaimer, the term of this patent is extended or adjusted under 35 U.S.C. 154(b) by 465 days.

This patent is subject to a terminal disclaimer.

(21) Appl. No.: 10/124,222

(22) Filed: Apr. 15, 2002

(65) Prior Publication Data

US 2003/0104415 A1 Jun. 5, 2003

Related U.S. Application Data

(63) Continuation of application No. 09/146,893, filed on Sep. 3, 1998, now Pat. No. 6,455,304, which is a continuation of application No. 08/270,581, filed on Jul. 1, 1994, now abandoned.

(51) Int. Cl.$^7$ ............................................. C12Q 1/68
(52) U.S. Cl. ........................................................ 435/6
(58) Field of Search ............................................ 435/6

(56) References Cited

U.S. PATENT DOCUMENTS

| | | | |
|---|---|---|---|
| 4,224,179 A | 9/1980 | Schneider | |
| 4,235,871 A | 11/1980 | Papahadjopoulos et al. | |
| 4,511,478 A | 4/1985 | Nowinski et al. | |
| 4,517,295 A | 5/1985 | Bracke et al. | |
| 4,708,861 A | 11/1987 | Popescu et al. | |
| 4,780,414 A | 10/1988 | Nimrod et al. | |
| 4,782,046 A | 11/1988 | Brown et al. | |
| 4,784,990 A | 11/1988 | Nimrod et al. | |
| 4,801,539 A | 1/1989 | Akasaka et al. | |
| 5,015,577 A | 5/1991 | Weigel et al. | |
| 5,023,175 A | 6/1991 | Hosoya et al. | |
| 5,071,751 A | 12/1991 | Morita et al. | |
| 5,948,900 A | 9/1999 | Yother et al. | |
| RE37,336 E | 8/2001 | Weigel et al. | |
| 6,423,514 B1 | 7/2002 | Briskin | |

FOREIGN PATENT DOCUMENTS

| | | |
|---|---|---|
| EP | 0144019 | 6/1985 |
| EP | 0244757 | 11/1987 |
| EP | 0036776 | 5/1988 |
| EP | 0195303 | 11/1989 |
| EP | 0266578 | 7/1993 |
| GB | 2249315 | 5/1992 |
| JP | 62032893 | 2/1987 |
| JP | 63094988 | 4/1988 |
| JP | 4-158796 | 6/1992 |
| WO | 91/03559 | 3/1991 |
| WO | 94/00463 | 1/1994 |
| WO | 95/24497 | 9/1995 |
| WO | 95/33067 | 11/1995 |
| WO | 97/20061 | 6/1997 |

OTHER PUBLICATIONS

DeAngelis et al., "Isolation of a *Streptococcus pyogenes* Locus That Directs Hyaluronan Biosynthesis in Acapsular Mutants and in Heterologous Bacteria," The Journal of Biological Chemistry, 268(20):14568–14571, 1993.

DeAngelis et al., "Molecular Cloning, Identification, and Sequence of The Hyaluronan Synthase Gene from Group A *Streptococcus pyogenes*," The Journal of Biological Chemistry, 268(26):19181–19184, 1993.

DeAngelis et al., "The *Streptococcus pyogenes* Hyaluronan Synthase: Sequence Comparison and Conservation Among Various Group A Strains," Biochemical and Biophysical Research Communications, 199(1):1–10, 1994.

Dougherty et al., "Molecular Characterization of a Locus Required for Hyaluronic Acid Capsule Production in Group A Streptococci," J. Exp. Med., 175:1291–1299, 1992.

Dougherty et al., "Molecular Characterization of hasA from an Operon Required for Hyaluronic Acid Synthesis in Group A Streptococci," The Journal of Biological Chemistry, 269(1):169–175, 1994.

Dougherty et al., "Molecular Characterization of hasB from an Operon Required for Hyaluronic Acid Synthesis in Group A Streptococci," The Journal of Biological Chemistry, 268(1):7118–7124, 1993.

Lansing et al., "Hyaluronate synthase: cloning and sequencing of the gene from Streptococcus sp.," Biochem. J., 289:179–184, 1993.

Laurent et al., "Hyaluronan," The FASEB Journal, 6:2397–2404, 1992.

Prehm, "Synthesis of hyaluronate in differentiated teratocarcinoma cells," Biochem J., 211:181–189, 1983.

Stoolmiller, and Dorfman, A., "The Biosynthesis of Hyaluronic Acid by Streptococcus," The Journal of Biological Chemistry, 244:236–246, 1969.

Trieu–Cuot et al., "Shuttle vectors containing a multiple cloning site and a lacZ• gene for conjugal transfer of DNA from *Escherichia coli* to Gram–positive bacteria," Gene, 102:99–104, 1991.

(List continued on next page.)

*Primary Examiner*—Robert A. Wax
(74) *Attorney, Agent, or Firm*—Dunlap, Codding and Rogers, P.C.

(57) ABSTRACT

Disclosed are DNA sequences encoding hyaluronic acid synthase that are employed to construct recombinant cells useful in the production of hyaluronate synthase and hyaluronic acid (HA). In preferred aspects, chromosomal DNA encoding the HA synthase gene, hasA, was cloned from a *Streptococcus pyogenes* genomic library. These vectors were used to transform host cells such as *E. coli* and acapsular *Streptococci* to produce hyaluronic acid. Resultant transformants were screened to identify colonies which have incorporated HA synthase DNA in a form that is being actively transcribed into the corresponding HA synthase enzyme. These colonies were selected and employed in the production of hyaluronic acid.

6 Claims, 7 Drawing Sheets

OTHER PUBLICATIONS van de Rijn et al., "Analysis of the Streptococcal Hyaluronic Acid Synthase Complex Using the Photoaffinity Probe 5–Azido–UDP–Clucuronic Acid," The Journal of Biological Chemistry, 267(34):24302–24306, 1992.

Wessels et al., "Hyaluronic acid capsule is a virulence factor for mucoid group A streptococci," Proc. Natl. Acad. Sci. USA, 88:8317–8321, 1991.

Ayala et al., "Modern Genetics," 1980, Benjamin/Cummings Publishing Co., Menlo Park, CA, p45.

"The Production of Capsules, Hyaluronic Acid and Hyaluronidase by Group A and Group C Streptococci", MacLennan, J. Gen. Microbiol., 14:134–142 (1956).

"The Isolation and Characterization of a Hyaluronidase Produced by a Capsulated Strain of Group C Streptoccus", MacLennan, J. Gen. Microbiol., 14:143–152 (1956).

"The Biosynthesis of Hyaluronic Acid by Group A Streptococcus", Markovitz et al., J. Biol. Chem., 234 (9):2343–2350 (1959).

"Biosynthesis of Hyaluronic Acid by Streptococcus", Sugahara et al., J. Biol. Chem., 254:6252–6261 (1979).

"Strains of *Escherichia coli* Carrying the Structural Gene for Histidyl–tRNA Synthetase on a High Copy–Number Plasmid," Eisenbeis, et al., Mol. Gen. Genet. 183:115–122 (1981).

"Streptococcal Hyaluronic Acid: Proposed Mechanisms of Degradation and Loss of Synthesis During Stationary Phase", Van de Rijn, J. Bacteriol., 156(3):1059–1065 (1983).

"Solubilization of Hyaluronic Acid Synthetic Activity from Streptococci and its Activation with Phospholipids", Triscott et al., J. Biol. Chem., 261(13):6004–6009 (1986).

"Isolation of Streptococcal Hyaluronate Synthase", Prehm et al., Biochem. J., 235:887–889 (1986).

"Isolation, Structure and Expression of Mammalian Genes for Histidyl–tRNA Synthetase," Tsui, et al., Nucleic Acids Research, vol. 15, No. 8, pp. 3349–3367, (1987).

"Molecular Fingerprinting of Pasteurella Multocida Associated with Progressive Atrophic Rhinitis in Swine Herds". Gardner et al. Database Medline on Diaolog, US Nat'l. Library of Medicine (Bethesda, MD, USA) No. 95161494, Abstract, J. Vet. Diagn. Invest. Oct. 1994. vol. 6, No. 4 pp. 442–447, see entire abstract.

The Elucidation of Novel Capsular Genotypes of Haemophilus Influenzae Type B with the Polymerase Chain Reaction. Leaves et al. J. Medical Microbiology. 1995, vol. 43, pp. 120–124, entire document.

"Homologs of the Xenopus Developmental Gene DG42 are Present in Zebrafish and Mouse and are Involved in the Synthesis of Nod–Like Chitin Oligosaccharides During Early Embryogenesis", Semino et al., Proc. Natl Acad. Sci. USA, 93:4548–4553 (1996).

"Enzymological Characterization of the Pasteurella Multocida Hyaluronic Acid Synthase", DeAngelis, Biochemistry, 35 (30): 9768–9771 (1996).

"Construction and Characterization of a Potential Live Oral Carrier–Based Vaccine Against Vibrio Chlolerae". Favre et al. Infection and Immunity. Sep. 1996. Vol. 64, No. 9 pagres 3565–3570, entire document.

"Molecular Cloning, Expression, and Characterization of the Authentic Hyaluronan Synthase from Group C *Streptococcus equisimilis*", Kumari and Weigel, J. Biol. Chem., 272(51): 32539–32546 (1997).

"Hyaluronan Synthases", Weigel et al., J. Biol. Chem., 272 (22): 13997–14000 (1997).

"Identification and Molecular Cloning of A Unique Hyaluronan Synthase From *Pasteurella multocida*", DeAngelis et al., J. Biol. Chem., 273(14): 8454–8458 (1998).

The Capsule Biosynthetic Locus of *Pasteurella multocida* A:1. Chung, et al. FEMS Microbiol. Lett. Sep. 15, 1998, vol. 166, No. 2, pp. 289–296, entire document.

```
AATTATTTTGGGATAATTTATTTAATATATATAAATAATTATCCTGATTTTCTTTTTCGGGGGAATTTT        -193
TTAATGGAAACACAATTTATTATTAAAAATATCTCTATATCTAGTTGACATTATTCTTATTTATATAAT        -121
ATTGAGGTCCTTTCTTCTTTCAAGGAATTAAAAGAAGAGGTGTAATTGTGCCTATTTTTAAAAAACTTTA        -49
                                   v p i f k k t  1

ATTGTTTTATCCTTTATTTTTTGATATCTATCTTGATTTATCTAAATATGTATCTATTGGAACATCAACT         24
i v l s f i f l i s l l i y l n M Y L F G T S T                               8

GTAGGAATTATGGAGTAATAATATTAATAACCTATCTAGTTATCAAACTTGGATTATCTTCCTTTATGAGCCA      96
V G I Y G V I L I T Y L V I K L G L S F L Y E P                              32

TTTAAAGGAAATCCACATGACTATAAAGTTGCTGCTGTAATTCCTTCGTAATGAAGATGCCGAGTCATTA       168
F K G N P H D Y K V A A V I P S Y N E D A E S L                              56

TTAGAAACACTTAAAAGTGTGTTAGCACAGACCTATCCGTTATCAGAAATTTATATTGTTGATGATGGGAGT       240
L E T L K S V L A Q T Y P L S E I Y I V D D G S                              80

TCAAAACACAGATGCAATACAATTAATTGAAGAGTATGTAAATAGAGAAGTGGATATTTGTCGAAACGTTATC     312
S N T D A I Q L I E E Y V N R E V D I C R N V I                             104

GTTCACCGTTCCCTTGTCAATAAAGGAAAAACGCCATGCTCAAGCGTGGGCATTTGAAAGATCTGACGCTGAC     384
V H R S L V N K G K R H A Q A W A F E R S D A D                             128

GTTTTTTTAACCGTAGACTCAGATACTTATATCCTATCCAAATGCCTTAGAAGAACTCCTAAAAAGCTTCAAT     456
V F L T V D S D T Y I Y P N A L E E L L K S F N                             152

GATGAGACAGTTTATGCTGCAACAGGACATTTGAATGCTAGAAACAGACAAACTAATCTATTAACGCGACTT     528
D E T V Y A A T G H L N A R N R Q T N L L T R L                             176
```

Fig. 7  1 of 2

```
ACAGATATCCGTTACGATAATGCCTTTGGGGTGGTGAGCGTGCTGCTCAATCATTAACAGGTAATATTTAGTT  600
 T  D  I  R  Y  D  N  A  F  G  V  V  E  R  A  A  Q  S  L  T  G  N  I  L  V   200

TGCTCAGGACCATTGAGTATTATCGACGTGAAGTGATTATTCCTAACTTAGAGCGCTATAAAAATCAAACA    672
 C  S  G  P  L  S  I  Y  R  R  E  V  I  I  P  N  L  E  R  Y  K  N  Q  T     224

TTCCTAGGTTTACCTGTGTTAGCATTGGGGATGATCGATGTGTTAACAAATTATGCTATTGATTAGGACGCACT 744
 F  L  G  L  P  V  S  I  G  D  D  D  R  C  L  T  N  Y  A  I  D  L  G  R  T  248

GTCTACCAATCAACAGCTAGATGTGATACTGATGTACCTTTCCAATTAAAAAGTTATTTAAAGCAACAAAAT   816
 V  Y  Q  S  T  A  R  C  D  T  D  V  P  F  Q  L  K  S  Y  L  K  Q  Q  N     272

CGATGGAATAAATCTTTTTTAGAGAATCTATTATTTCGTTAAAAAAATTCTTTCTAATCCCATCGTTGCC     888
 R  W  N  K  S  F  F  R  E  S  I  I  S  V  K  K  I  L  S  N  P  I  V  A     296

TTATGGACTATTTCGAAGTCGTTATGTTTATGATGTTGATTGTCGCAATTGGGAATCTTTTGTTTAATCAA    960
 L  W  T  I  F  E  V  V  M  F  M  M  L  I  V  A  I  G  N  L  F  N  Q         320

GCTATTCAATTAGACCTTATTAAACTTTTTGCCTTTTTTGCTTTTATCCATCATCTTTATCGTTGCTTTATGTCGTAAT 1032
 A  I  Q  L  D  L  I  K  L  F  A  F  L  S  I  I  F  I  V  A  L  C  R  N       344

GTTCATTATATGGTCAAACATCCTGCTAGTTTTTTTGTTATCTCCTCGTATGGAATATTACACTTGTTTGTC   1104
 V  H  Y  M  V  K  H  P  A  S  F  L  L  S  P  L  Y  G  I  L  H  L  F  V      368

TTACAGCCCCTAAAACTTTATTCTTTATGCACCATTAAAAATACGGAATGGGAACACGTAAAAAGTCACT    1176
 L  Q  P  L  K  L  Y  S  L  C  T  I  K  N  T  E  W  G  T  R  K  K  V  T      392

ATTTTAAATAATATATGCATCGAGTAGTTAGAGAGTAATTTTATGAAAATAGCAGTTGCTGGATCAG        1248
                                    M  K  I  A  V  A  G  S                    395
 I  F  K  -
```

Fig. 7 2 of 2

HYALURONATE SYNTHASE GENE AND USES THEREOF

CROSS REFERENCE TO RELATED APPLICATIONS

This application is a continuation of U.S. patent application Ser. No. 09/146,893, filed Sep. 3, 1998, now U.S. Pat. No. 6,455,304 entitled "HYALURONATE SYNTHASE GENE AND USES THEREON;" which is a continuation of U.S. patent application Ser. No. 08/270,581, filed Jul. 1, 1994, entitled "HYALURONATE SYNTHASE GENE AND USES THEREON," now abandoned.

The government owns certain rights in the present invention pursuant to grant number GM35978 from the National Institutes of Health.

BACKGROUND OF THE INVENTION

1. Field of the Invention

The present invention relates to a nucleic acid encoding the enzyme hyaluronate synthase, and to the use of this nucleic acid in the preparation of recombinant cells for the production of the hyaluronate synthase enzyme and hyaluronic acid. Hyaluronate is also known as hyaluronic acid or hyaluronan.

2. Description of the Related Art

The incidence of streptococcal infections is a major health and economic problem worldwide, particularly in developing countries (Rotta, 1988). One reason for this is due to the ability of Streptococcal bacteria to grow undetected by the body's phagocytic cells (i.e., macrophages and polymorphonuclear cells (PMNs). These cells are responsible for recognizing and engulfing foreign microorganisms. One effective way the bacteria evade surveillance is by coating themselves with polysaccharide capsules, such as hyaluronic acid (HA) capsules. (Kendall et al., 1937). Since HA is generally nonimmunogenic (Quinn and Singh, 1957), the encapsulated bacteria do not elicit an immune response and are, therefore, not targeted for destruction. Moreover, the capsule exerts an antiphagocytic effect on PMNs in vitro (Hirsch, et al., 1960) and prevents attachment of Streptococcus to macrophages (Whitnack, et al., 1981). Precisely because of this, in group A and group C Streptococci, the HA capsules are major virulence factors in natural and experimental infections (Kass, et al., 1944; Wessels, et al., 1991). Group A Streptococcus are responsible for numerous human diseases including pharyngitis, impetigo, deep tissue infections, rheumatic fever and a toxic shock-like syndrome (Schaechter, et al., 1989). The group C Streptococcus equisimilis is responsible for osteomyelitis (Barson, 1986), pharyngitis (Benjamin, et al., 1976), brain abscesses (Dinn, 1971), and pneumonia (Rizkallah, et al., 1988; Siefkin, et al., 1983).

Structurally, HA is a high molecular weight linear polysaccharide of repeating disaccharide units consisting of N-acetylglucosamine (GlcNAc) and glucuronic acid (GlcA) (Laurent and Fraser, 1992). HA is the only glycosaminoglycan synthesized by both mammalian and bacterial cells particularly groups A and C Streptococci. Some Streptococcus strains make HA which is secreted into the medium as well as HA capsules. The mechanism by which these bacteria synthesize HA is of interest since the production of the HA capsule is a very efficient and clever way that Streptococci use to evade surveillance by the immune system.

HA is synthesized by both mammalian and Streptococcus cells by the enzyme hyaluronate synthase, that has been localized to the plasma membrane of Streptococcus (Markovitz, et al., 1962). The synthesis of HA in these organisms is a multi-step process. Initiation involves binding of an initial precursor, UDP-GlcNAc or UDP-GlcA. This is followed by elongation which involves alternate addition of the two sugars to the growing oligosaccharide chain. The growing polymer is extruded across the bacterial plasma membrane region of the cell wall and into the extracellular space. Although the HA biosynthetic system was one of the first membrane heteropolysaccharide synthetic pathways studied, the mechanism of HA synthesis is still not understood. This may be because in vitro systems developed to date are inadequate in that de novo biosynthesis of HA has not been accomplished. Chain elongation but not new chain initiation occurs.

The direction of HA polymer growth is a matter of disagreement. Addition of the monosaccharides could be to the reducing (Prehm, 1983) or nonreducing (Stoolmiller, et al., 1969) end of the growing HA chain. In addition, other questions that need to be addressed are (i) whether nascent chains are linked covalently to a protein, to UDP or to a lipid intermediate, (ii) whether chains are initiated using a primer, and (iii) the mechanism by which the mature polymer is extruded through the plasma membrane of the Streptococcus. Understanding the mechanism of HA biosynthesis may allow development of alternative strategies to control Streptococcal infections by interfering in the process.

Group C S. equisimilis strain D181 synthesizes and secretes HA. Investigators have used this strain and group A strains, such as A111, to study the biosynthesis of HA and to characterize the HA-synthesizing activity in terms of its divalent cation requirement (Stoolmiller, et al., 1969), precursor (UDP-GlcNAc and UDP-GlcUA) utilization (Ishimoto, et al., 1967; Markovitz, et al., 1959), and optimum pH (Stoolmiller, et al., 1969). The HA synthase enzyme has been studied for approximately 30 years, but has not yet been identified or purified. Although a 52-kD protein has been putatively suggested as the HA synthase (Prehm, et al., 1986), this report is now known to be in error. Furthermore, no one has successfully purified to homogeneity an active enzyme. Moreover, it's not clear whether a bona fide HA synthase molecule is all that is needed for the generation of hyaluronic acid, or whether it might act in concert with other cellular components or subunits. Thus, totally ex vivo methods of producing HA have not been forthcoming.

Typically, HA has been prepared commercially by isolation from either rooster combs or extracellular media from Streptococcal cultures. One method which has been developed for preparing HA is through the use of cultures of HA-producing streptococcal bacteria. U.S. Pat. No. 4,517,295, describes such a procedure, wherein HA-producing Streptococci are fermented under anaerobic conditions in a $CO_2$-enriched growth medium. Under these conditions, HA is produced and can be extracted from the broth. It is generally felt that isolation of HA from rooster comb is laborious and difficult, since one starts with HA in a less pure state. The advantage of isolation from rooster comb is that the HA produced is of higher molecular weight. However, preparation of HA by bacterial fermentation is easier, since the HA is of higher purity to start with. Usually, however, the molecular weight of HA produced in this way is smaller than that from rooster combs. Therefore, a technique that would allow the production of high molecular weight HA by bacterial fermentation would be an improvement over existing procedures.

High molecular weight HA has a wide variety of useful applications—ranging from cosmetics to eye surgery (Laurent and Fraser, 1992). Due to its potential for high viscosity and its high biocompatibility, HA finds particular application in eye surgery as a replacement for vitreous fluid. HA has also been used to treat racehorses for traumatic arthritis by intra-articular injections of HA, in shaving cream as a lubricant, and in a variety of cosmetic products due to its physiochemical properties of high viscosity and its ability to retain moisture for long periods of time. In general, the higher molecular weight the HA that is employed the better. This is because HA solution viscosity increases with the average molecular weight of the individual HA polymer molecules in the solution. Unfortunately, very high molecular weight HA, such as that ranging up to $10^7$, has been difficult to obtain by currently available isolation procedures.

To address these or other difficulties, there is a need for new methods and constructs that can be used to produce HA having one or more improved properties such as greater purity or ease of preparation. In particular, there is a need to develop methodology for the production of larger amounts of relatively higher molecular weight and purity HA than is available from current technology. The present invention addresses one or more shortcomings in the art through the application of recombinant DNA technology.

SUMMARY OF THE INVENTION

The present invention involves the application of recombinant DNA technology to solving one or more problems in the art of hyaluronic acid preparation. These problems are addressed through the isolation and use of a DNA segment encoding all or a portion of the hyaluronate synthase gene, the gene responsible for HA chain biosynthesis. The gene was cloned from DNA of an appropriate microbial source and engineered into useful recombinant constructs for the preparation of HA and for the preparation of large quantities of the HA synthase enzyme itself.

The present invention, in a general and overall sense, concerns the isolation and characterization of a hyaluronate or hyaluronic acid synthase gene, as may be used for the polymerization of glucuronic acid and N-acetylglucosamine into the glycosaminoglycan hyaluronic acid. The present inventors have identified the hasA locus and have determined the sequence encoding the Hyaluronic acid synthase (HA synthase) gene from *Streptococcus*. The hasA gene product, HasA, has been expressed in homologous and heterologous cells, can be used to isolate hyaluronic acid synthase, and can be used for the production of hyaluronic acid. The hasA gene also provides a new probe to assess the potential of bacterial specimens to produce hyaluronic acid.

The present invention encompasses a novel gene, hasA. The expression of this gene correlates with virulence of *Streptococcal* strains, by providing a means of escaping immune surveillance. The term, "hyaluronic acid synthase", "hyaluronate synthase", "hyaluronan synthase" and "HA synthase", are used interchangeably to describe an enzyme that polymerizes a glycosaminoglycan polysaccharide chain composed of alternating glucuronic acid and N-acetylglucosamine sugars.

Through the application of techniques and knowledge set forth herein, those of skill in the art will be able to obtain nucleic acid segments encoding an HA synthase gene. Through isolation of the HA gene, from whatever source is chosen, one will have the ability to realize significant advantages such as an ability to manipulate the host that is chosen to express the HA synthase gene, the fermentation environment chosen for HA production, as well as genetic manipulation of the underlying gene. As those of skill in the art will recognize, in light of the present disclosure, this will provide additional significant advantages both in the ability to control the expression of the gene and in the nature of the gene product that is realized.

Accordingly, the invention is directed to the isolation of DNA that comprises the HA synthase gene, whether it be from prokaryotic or eukaryotic sources. This is possible because the enzyme, and indeed the gene, is one found in both eukaryotes and some prokaryotes. Typical prokaryotic sources will include Group A or Group C *Streptococcus* sources such as *S. pyogenes*, *S. equisimilis*, or *S. zooepidemicus*. Eukaryotes are also known to produce HA (Ng and Schwartz, 1989) and thus have HA synthase genes that may be employed in connection with the invention. For example, it is known that HA is produced in rooster combs by mesodermal cells of the rooster. These cells can be employed to isolate starting mRNA for the production of cDNA libraries by well known techniques, which can subsequently be screened by novel screening techniques set forth herein. Other eukaryotic sources that can be employed include synovial chondrocytes and fibroblasts, dermal fibroblasts, and even trabecular-meshwork cells of the eye.

HA synthase-encoding nucleic acid segments of the present invention are defined as being isolated free of total chromosomal or genomic DNA such that they may be readily manipulated by recombinant DNA techniques. Accordingly, as used herein, the phrase "substantially purified DNA segment" refers to a DNA segment isolated free of total chromosomal or genomic DNA and retained in a state rendering it useful for the practice of recombinant techniques, such as DNA in the form of a discrete isolated DNA fragment, or a vector (e.g., plasmid, phage or virus) incorporating such a fragment.

A preferred embodiment of the present invention is a purified nucleic acid segment encoding HA synthase, wherein the segment encodes a protein having an amino acid sequence in accordance with SEQ ID NO:2, or that is capable of hybridizing to the nucleotide sequence of SEQ ID NO:1 under standard hybridization conditions as described herein. The nucleotide segment of the present invention is a purified nucleic acid segment, further defined as including a nucleotide sequence as shown in FIG. 7, and in accordance with SEQ ID NO:1.

In a more preferred embodiment the purified nucleic acid segment consists essentially of the nucleotide sequence of SEQ ID NO:1. As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains an hasA coding sequence yet is isolated away from, or purified free from, total genomic DNA, for example, total *Streptococcus pyogenes* or, for example, mammalian host genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified hasA gene refers to a DNA segment including hasA coding sequences isolated substantially away from other naturally occurring genes or protein encoding sequences. In this respect, the term "gene" is used for simplicity to refer to a functional protein, polypeptide or peptide encoding unit.

As will be understood by those in the art, this functional term includes genomic sequences, cDNA sequences or combinations thereof. "Isolated substantially away from other coding sequences" means that the gene of interest, in this case hasA, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the HA synthase gene from prokaryotes such as S. pyogenes or S. equisimilis. One such advantage is that, typically, eukaryotic enzymes may require significant post-translational modifications that can only be achieved in a eukaryotic host. This will tend to limit the applicability of any eukaryotic HA synthase gene that is obtained. Moreover, those of skill will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library and (b) the ease of manipulation because the overall size of the coding region of a prokaryotic gene is significantly smaller due to the absence of introns. Furthermore, if the product of the HA synthase gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned. For example, in streptococcal hosts, the preferred control region is the homologous control region associated with the structural gene in its natural state. The homologous control region, in fact, may be coisolated directly with the isolation of the HA synthase structural gene itself through the practice of certain preferred techniques disclosed herein.

In particular embodiments, the invention concerns isolated DNA segments and recombinant vectors incorporating DNA sequences which encode an hasA gene, that includes within its amino acid sequence an amino acid sequence in accordance with SEQ ID NO:2. Moreover, in other particular embodiments, the invention concerns isolated DNA segments and recombinant vectors incorporating DNA sequences which encode a gene that includes within its amino acid sequence the amino acid sequence of an hasA gene corresponding to Streptococcus pyogenes hasA. Naturally, where the DNA segment or vector encodes a full length HasA protein, or is intended for use in expressing the HasA protein, the most preferred sequences are those which are essentially as set forth in SEQ ID NO:2.

Nucleic acid segments having HA synthase activity may be isolated by the methods described hereinabove. The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein, as a gene having a sequence essentially as set forth in SEQ ID NO:2, and that is associated with the ability of Streptococcus to produce HA and a hyaluronic acid coat. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:2 will be sequences which are "essentially as set forth in SEQ ID NO:2".

Another preferred embodiment of the present intention is a purified nucleic acid segment that encodes a protein in accordance with SEQ ID NO:2, further defined as a recombinant vector. As used herein the term, "recombinant vector", refers to a vector that has been modified to contain a nucleic acid segment that encodes an HasA protein, or fragment thereof. The recombinant vector may be further defined as an expression vector comprising a promoter operatively linked to said HasA encoding nucleic acid segment.

A further preferred embodiment of the present invention is a host cell, made recombinant with a recombinant vector comprising an hasA gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding hasA, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

Where one desires to use a host other than Streptococcus, as may be used to produce recombinant HA synthase, it may be advantageous to employ a prokaryotic system such as E. coli, B. subtilis, Lactococcus sp., or even eukaryotic systems such as yeast or Chinese hamster ovary, African green monkey kidney cells, VERO cells, or the like. Of course, where this is undertaken, it will generally be desirable to bring the HA synthase gene under the control of sequences which are functional in the selected alternative host. The appropriate DNA control sequences, as well as their construction and use, are generally well known in the art as discussed in more detail herein below.

In preferred embodiments, the HA synthase-encoding DNA segments further include DNA sequences, known in the art functionally as origins of replication or "replicons", which allow replication of contiguous sequences by the particular host. Such origins allow the preparation of extra-chromosomally localized and replicating chimeric segments or plasmids, to which HA synthase DNA sequences are ligated. In more preferred instances, the employed origin is one capable of replication in Streptococcus hosts. However, for more versatility of cloned DNA segments, it may be desirable to alternatively or even additionally employ origins recognized by other host systems whose use is contemplated (such as in a shuttle vector)

The isolation and use of other replication origins such as the SV40, polyoma or bovine papilloma virus origins, which may be employed for cloning in a number of higher organisms, are well known (Fiers, et al., 1978) In certain embodiments, the invention may thus be defined in terms of a recombinant transformation vector which includes the HA synthase gene sequence together with an appropriate replication origin and under the control of selected control regions.

In accordance with the present invention, the HA synthase gene, when from a prokaryotic source such as a *Streptococcal* source, is obtained by the following general steps. First, the genetic loci are identified by transposon insertional mutagenesis. One such transposon system is the TN916, obtainable from the transposon donor strain *E. faecalis* CG110, which was used to mutate the mucoid strain of *Streptococcus pyogenes* S43. Mutants were isolated and the genomic DNA surrounding the transposon was sequenced and used to derive oligonucleotides for use in cloning the wild-type gene. Phage libraries were screened, and two clones, λ1X and λ2Y, were obtained that contained the predicted sequence. The locus was characterized by restriction mapping and southern blot analysis.

Thus, although the present invention is exemplified in terms of clones screened via transposon mediated mutagenesis, it will be appreciated by those of skill in the art that other means may be used to obtain the hasA gene, in light of the present disclosure. For example, polymerase chain reaction produced DNA fragments may be obtained which contain full complements of genes from a number of sources, including other strains of *Streptococcus* or from eukaryotic sources, such as CDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HA synthase.

Once the DNA has been isolated it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pBluescript™, pSA3, lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* are employed.

Vectors such as these, exemplified by the pSA3 vector of Dao and Ferretti (Dao, et al., 1985) or the pAT19 vector of Trieu-Cuot, et al. (1991), allow one to perform clonal colony selection in an easily manipulated host such as *E. coli*, followed by subsequent transfer back into a *Lactococcus* or *Bacillus* strain for production of HA. This is advantageous in that one can augment the *Lactococcus* or *Bacillus* strain's ability to synthesize HA through gene dosaging (i.e., providing extra copies of the HA synthase gene by amplification) and/or inclusion of additional genes to increase the availability of HA precursors. The inherent ability of *Streptococci* to synthesize HA can also be augmented through the formation of extra copies, or amplification, of the plasmid that carries the HA synthase gene. This amplification can account for up to a 10-fold increase in plasmid copy number and, therefore, the HA synthase gene copy number.

Another procedure that would further augment HA synthase gene copy number is the insertion of multiple copies of the gene into the plasmid. This extra amplification would be especially feasible, since the bacterial HA synthase gene size is small. In any event, the chromosomal DNA-ligated vector is employed to transfect the host that is selected for clonal screening purposes such as *E. coli*, through the use of a vector that is capable of expressing the inserted DNA in the chosen host.

Where a eukaryotic source such as dermal or synovial fibroblasts or rooster comb cells is employed, one will desire to proceed initially by preparing a cDNA library. This is carried out first by isolation of mRNA from the above cells, followed by preparation of double stranded cDNA using an enzyme with reverse transcriptase activity and ligation with the selected vector. Numerous possibilities are available and known in the art for the preparation of the double stranded cDNA, and all such techniques are believed to be applicable. A preferred technique involves reverse transcription. Once a population of double stranded cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as λgt11 or λgt12, for the cloning and expression screening of cDNA clones.

Due to the general absence of correct information regarding the HA synthase enzyme, traditional approaches to clonal screening, such as oligonucleotide hybridization or immunological screening, was not available. Accordingly, it was necessary for the inventors to use an alternative approach based on phenotype to screen and select for the HA synthase that rely on abrogating expression of HA synthase activity. The methods which were developed can be applied to screen the selected host, regardless of whether a eukaryotic or prokaryotic gene is sought. One method involves the application of a dye exclusion technique to identify clones which contain HA. The typical dye employed, India ink, is excluded from an HA capsule and allows visualization of HA by negative staining. A second method involves positive staining, such as with Alcian Blue, to identify HA producing clones. Alcian Blue binds to and stains polyanionic molecules such as HA (Scott, et al., 1964). However, in that India ink or Alcian Blue is not entirely specific for HA, the present inventors employed additional screening methods as described in Examples I and II.

A variety of additional screening and validation procedures are also set forth herein that can variously be employed to identify the presence of either the HA enzyme or its HA product as a means for identifying positive clones or negative clones (mutants). These procedures included the use of Percoll gradient centrifugation and the ability of membrane fractions from candidate clones to incorporate authentic radiolabeled sugar nucleotides into high molecular weight HA.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1", is used in the same sense as described above and means that the nucleic acid sequence substantially corresponds to a portion of SEQ ID No:1, and has relatively few codons which are not identical, or functionally equivalent, to the codons of SEQ ID NO:1. The term "functionally equivalent codon" is used herein to refer to codons that encode the same amino acid, such as the six codons for arginine or serine, as set forth in Table I, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes.

Allowing for the degeneracy of the genetic code, sequences which have between about 70% and about 80%; or more preferably, between about 80% and about 90%; or even more preferably, between about 90% and about 99%; of nucleotides which are identical to the nucleotides of SEQ ID NO:1 will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under relatively stringent conditions. Suitable relatively stringent hybridization conditions will be well known to those of skill in the art and are clearly set forth herein, for example conditions for use with southern and northern blot analysis.

The term "standard hybridization conditions" as used herein, is used to describe those conditions under which substantially complementary nucleic acid segments will form standard Watson-Crick base-pairing. A number of factor are known that determine the specificity of binding or hybridization, such as pH, salt concentration, the presence of chaotropic agents (e.g. formamide and dimethyl sulfoxide), the length of the segments that are hybridizing, and the like.

For use with the present invention, standard hybridization conditions for relatively large segments, that is segments longer than about 100 nucleotides, will include a hybridization mixture having between about 0.3 to 0.6 M NaCl, a divalent cation chelator (e.g. EDTA at about 0.05 mM to about 0.5 mM), and a buffering agent (e.g. Na2PO4 at about 10 mM to 100 mM, pH 7.2), at a temperature of about 65° C. The preferred conditions for hybridization are a hybridization mixture comprising 0.5 M NaCl, 5 mM EDTA, 0.1 M $Na_2PO_4$, pH 7.2 and 1% N-lauryl sarcosine, at a temperature of 65° C. Naturally, conditions that affect the hybridization temperature, such as the addition of chaotropic agents, such as formamide, will be known to those of skill in the art, and are encompassed by the present invention.

When it is contemplated that shorter nucleic acid segments will be used for hybridization, for example fragments between about 14 and about 100 nucleotides, salt and temperature conditions will be altered to increase the specificity of nucleic acid segment binding. Preferred conditions for the hybridization of short nucleic acid segments include lowering the hybridization temperature to about 37° C., and increasing the salt concentration to about 0.5 to 1.5 M NaCl with 1.5 M NaCl being particularly preferred.

TABLE I

CODON DEGENERACY

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Naturally, the present invention also encompasses DNA segments which are complementary, or essentially complementary, to the sequence set forth in SEQ ID NO:1. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1 under relatively stringent conditions such as those described herein in Example III.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, such as about 10 to 15 or 20, 30, or 40 or so nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

A preferred embodiment of the present invention is a nucleic acid segment which comprises at least a 10–14 nucleotide long stretch which corresponds to, or is complementary to, the nucleic acid sequence of SEQ ID NO:1. In a more preferred embodiment the nucleic acid is further defined as comprising at least a 20 nucleotide long stretch, a 30 nucleotide long stretch, 50 nucleotide long stretch, 100 nucleotide long stretch, a 200 nucleotide long stretch, a 500 nucleotide long stretch, a 1000 nucleotide long stretch, a 1500 nucleotide long stretch, or at least a 1441 nucleotide long stretch which corresponds to, or is complementary to, the nucleic acid sequence of SEQ ID NO:1. The nucleic acid segment may be further defined as having the nucleic acid sequence of SEQ ID NO:1.

A related embodiment of the present invention is a nucleic acid segment which comprises at least a 10–14 nucleotide long stretch which corresponds to, or is complementary to, the nucleic acid sequence of SEQ ID NO:1, further defined as comprising a nucleic acid fragment of up to 10,000 basepairs in length. A more preferred embodiment if a nucleic acid fragment comprising from 14 nucleotides of SEQ ID NO:1 up to 5,000 basepairs in length, 3,000 basepairs in length, 1,000 basepairs in length, 500 basepairs in length, or 100 basepairs in length.

Naturally, it will also be understood that this invention is not limited to the particular nucleic acid and amino acid sequences of SEQ ID NOS:1 and 2. Recombinant vectors and isolated DNA segments may therefore variously include the hasA coding regions themselves, coding regions bearing selected alterations or modifications in the basic coding region, or they may encode larger polypeptides which nevertheless include hasA-coding regions or may encode biologically functional equivalent proteins or peptides which have variant amino acids sequences.

The DNA segments of the present invention encompass biologically functional equivalent HasA proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques e.g., to introduce improvements to the enzyme activity or to antigenicity of the HasA protein or to test HasA mutants in order to examine HA synthase activity at the molecular level.

A preferred embodiment of the present invention is a purified composition comprising a polypeptide having an amino acid sequence in accordance with SEQ ID NO:2. The term "purified" as used herein, is intended to refer to an HasA protein composition, wherein the HasA protein is purified to any degree relative to its naturally-obtainable state, i.e., in this case, relative to its purity within a prokaryotic cell extract. A preferred cell for the isolation of HasA protein is a *Streptococcus pyogenes* cell, however, HasA protein may also be isolated from other members of the *Streptococcus* genus, patient specimens, recombinant cells, infected tissues, isolated subpopulation of tissues that contain high levels of hyaluronate in the extracellular matrix, and the like, as will be known to those of skill in the art, in light of the present disclosure. A purified HasA protein composition therefore also refers to a polypeptide having the amino acid sequence of SEQ ID NO:2, free from the environment in which it may naturally occur.

If desired, one may also prepare fusion proteins and peptides, e.g., where the HasA protein coding regions are aligned within the same expression unit with other proteins or peptides having desired functions, such as for purification or immunodetection purposes (e.g., proteins which may be purified by affinity chromatography and enzyme label coding regions, respectively).

Turning to the expression of the hasA gene whether from genomic DNA, or a cDNA one may proceed to prepare an expression system for the recombinant preparation of HasA protein. The engineering of DNA segment(s) for expression in a prokaryotic or eukaryotic system may be performed by techniques generally known to those of skill in recombinant expression. For example, one may prepare a HasA-GST (glutathione-S-transferase) fusion protein that is a convenient means of bacterial expression. However, it is believed that virtually any expression system may be employed in the expression of HasA.

HasA may be successfully expressed in eukaryotic expression systems, however, the inventors aver that bacterial expression systems can be used for the preparation of HasA for all purposes. The cDNA for HasA may be separately expressed in bacterial systems, with the encoded proteins being expressed as fusions with β-galactosidase, avidin, ubiquitin, *Schistosoma japonicum* glutathione S-transferase, maltose-binding protein, polyhistidine-tags, epitope-tags (e.g., myc and FLAG) and the like. It is believed that bacterial expression will ultimately have advantages over eukaryotic expression in terms of ease of use and quantity of materials obtained thereby.

It is proposed that transformation of host cells with DNA segments encoding HasA will provide a convenient means for obtaining an HasA protein. It is also proposed that cDNA, genomic sequences, and combinations thereof, are suitable for eukaryotic expression, as the host cell will, of course, process the genomic transcripts to yield functional mRNA for translation into protein.

Another embodiment of the present invention is a method of preparing a protein composition comprising growing recombinant host cell comprising a vector that encodes a protein which includes an amino acid sequence in accordance with SEQ ID NO:2. The host cell will be grown under conditions permitting nucleic acid expression and protein production followed by recovery of the protein so produced. The production of HA synthase and HA, including: the host cell, conditions permitting nucleic acid expression, protein production and recovery will be known to those of skill in the art in light of the present disclosure of the hasA gene, and the hasA gene protein product HasA, and by the methods described in Examples III, IV, and V.

Preferred hosts for the expression of hyaluronic acid are prokaryotes, such as *S. pyogenes, S. equisimilis*, and other suitable members of the *Streptococcus* species. However, it is also contemplated that HA may be synthesized by heterologous host cells expressing HA synthase, such as species members of the *Bacillus, Salmonella, Pseudomonas, Enterococcus,* or even *Escherichia* genus. A most preferred host for expression of the HA synthase of the present invention is a bacteria transformed with the hasA gene of the present invention, such as *Lactococcus, Bacillus subtilis* or *S. pyogenes.*

It is similarly believed that almost any eukaryotic expression system may be utilized for the expression of hasA e.g., baculovirus-based, glutamine synthase-based, dihydrofolate reductase-based systems, SV-40 based, adenovirus-based, cytomegalovirus-based, and the like, could be employed. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the hasA gene, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of hasA in accordance herewith. Examples of preferred cell lines for expressing the HA synthase gene of the present invention include cell lines typically employed for eukaryotic expression such as 239, AtT-20, HepG2, VERO, HeLa, CHO, WI 38, BHK, COS-7, RIN and MDCK cell lines.

This will generally include the steps of providing a recombinant host bearing the recombinant DNA segment encoding the HA synthase enzyme and capable of expressing the enzyme; culturing the recombinant host in media under conditions that will allow for transcription of the cloned HA gene and appropriate for the production of the hyaluronic acid; and separating and purifying the HA synthase enzyme or the secreted hyaluronic acid from the recombinant host.

Generally, the conditions appropriate for expression of the cloned HA synthase gene will depend upon the promoter, the vector, and the host system that is employed. For example, where one employs the lac promoter, one will desire to induce transcription through the inclusion of a material that will stimulate lac transcription, such as IPTG. Where other promoters are employed, different materials may be needed to induce or otherwise up-regulate transcription. In addition, to obtaining expression of the synthase, one will preferably desire to provide an environment that is conducive to HA synthesis by including appropriate genes encoding enzymes needed for the biosynthesis of sugar nucleotide precursors, and by using growth media containing substrates for the precursor-supplying enzymes, such N-acetylglucosamine (GlcNAc) and glucose (Glc).

One may further desire to incorporate the gene in a host which is defective in the enzyme hyaluronidase, so that the product synthesized by the enzyme will not be degraded in the medium. Furthermore, a host would be chosen to optimize production of HA. For example, a suitable host would be one that produced large quantities of the sugar nucleotide precursors to support the HA synthase enzyme and allow it to produce large quantities of HA. Such a host may be found naturally or may be made by a variety of techniques including mutagenesis or recombinant DNA technology. The genes for the sugar nucleotide synthesizing enzymes, particularly the UDP-Glc dehydrogenase required to produce UDP-GlcA, could also be isolated and incorporated in a vector along with the HA synthase gene. A preferred embodiment of the present invention is a host containing these ancillary recombinant genes and the amplification of these gene products thereby allowing for increased production of HA.

In the case where production of HA synthase is desired, the enzyme is preferably synthesized in bacteria using the T7 expression system (Studier, et al., 1990). pT5 plasmids containing the HA synthase gene inserted adjacent to the phil0 promoter are transformed into *E. coli* stain BL21(DE3) pLysS. In this strain the T7 gene encoding the bacteriophage RNA polymerase is under control of the *E. coli* lacZ promoter. Therefore, the polymerase can be induced by IPTG and transcription of the HA synthase gene is, in turn, induced from the φ10 promoter of the pT5 vector.

The means employed for culturing of the host cell is not believed to be particularly crucial. For useful details, one may wish to refer to the disclosure of U.S. Pat. Nos. 4,517,295; 4,801,539; 4,784,990; or 4,780,414; all incorporated herein by reference. Where a prokaryotic host is employed, such as *S. pyogenes* or *S. equisimilis*, one may desire to employ a fermentation of the bacteria under anaerobic conditions in $CO_2$-enriched broth growth media. This allows for a greater production of HA than under aerobic conditions. Another consideration is that *Streptococcal* cells grown anaerobically do not produce pyrogenic exotoxins. Appropriate growth conditions can be customized for other prokaryotic hosts, as will be known to those of skill in the art, in light of the present disclosure.

Once the appropriate host has been constructed, and cultured under conditions appropriate for the production of HA, one will desire to separate the HA so produced. Typically, the HA will be secreted or otherwise shed by the recombinant organism into the surrounding media, allowing the ready isolation of HA from the media by known techniques. For example, HA can be separated from the media by filtering and/or in combination with precipitation by alcohols such as ethanol. Other precipitation agents include organic solvents such as acetone or quaternary organic ammonium salts such as cetyl pyridinium chloride (CPC).

A preferred technique for isolation of HA is described in U.S. Pat. No. 4,517,295 in which the organic carboxylic acid, trichloroacetic acid, is added to the bacterial suspension at the end of the fermentation. The trichloroacetic acid causes the bacterial cells to clump and die and facilitates the ease of separating these cells and associated debris from HA, the desired product. The clarified supernatant is concentrated and dialyzed to remove low molecular weight contaminants including the organic acid. The aforementioned procedure utilizes Millipore(tm) filtration through filter cassettes containing 0.22 μm pore size filters. Diafiltration is continued until the conductivity of the solution decreases to approximately 0.5 mega-ohms.

The concentrated HA is precipitated by adding an excess of reagent grade ethanol or other organic solvent and the precipitated HA is then dried by washing with ethanol and vacuum dried, lyophilized or spray dried to remove alcohol. The HA can then be redissolved in a borate buffer, pH 8, and precipitated with CPC or certain other organic ammonium salts such as CETAB, a mixed trimethyl ammonium bromide solution at 4 degree(s) C. The precipitated HA is recovered by coarse filtration, resuspended in 1 M NaCl, diafiltered and concentrated as further described in the above referenced patent. The resultant HA is filter sterilized and ready to be converted to an appropriate salt, dry powder or sterile solution, depending on the desired end use.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7: Nucleotide and Deduced Protein Sequence of the HA Synthase gene, hasA. The DNA sequence surrounding the HA synthase ORF was determined on both strands with Sequenase. The standard deduced start codon for a protein (ATG) is indicated as the first amino acid in this figure. This putative start codon (ATG) is marked as position +1. Alternate start codons (Gren, 1984) indicated in bold-face (GTG at −72 or TTG at −27 and −15) are present in-frame upstream from this ATG. The additional amino acids comprising HasA, if alternative start codons are used, are shown in lower case. Hydrophobic stretches predicted to be membrane-associated are underlined and Cys residues are shown stippled. The beginning of HasB (Dougherty and van de Rijn, 1993) is also depicted at the lower right. The sequence is in the GenBank database under Accession No. L20853.

Figure 1:
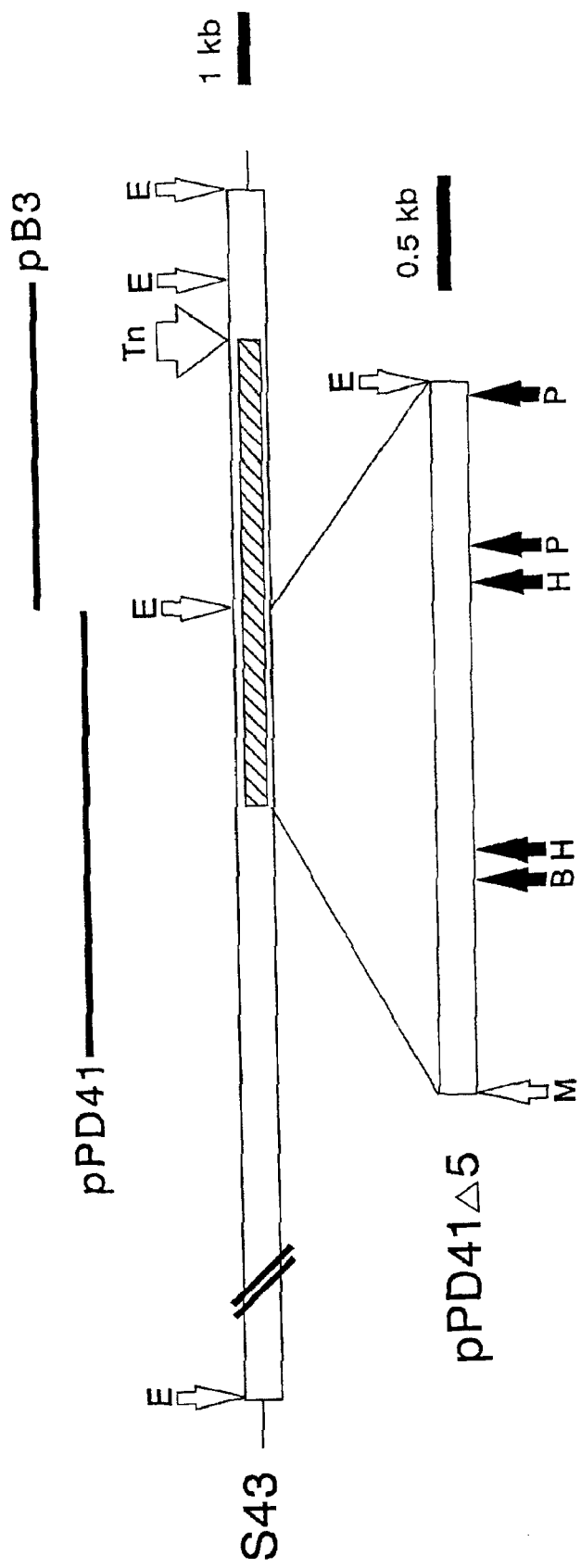
FIG. 1: Restriction map of the *streptococcal* HA biosynthesis locus. EcoRI (E) restriction sites on the wild-type S43 chromosome are illustrated with respect to the relevant Tn insertion and the minimal extent of the associated deletion (hatched box). The region of DNA capable of directing HA synthesis in mutants and heterologous species, pPD41Δ5 is shown. Two HindIII (H), two PstI (P) and one BglII (B) sites were found. KpnI, BamHI, SalI, SacI, SmaI, SphI, and XbaI did not cut the pPD41Δ5 insert. The multiple cloning site (M) is the result of fusion of the deleted, blunt ended DNA and the pAT19 M. The inserts of the initial clones pB3 and pPD41 are shown above the genomic map. The large EcoRI fragment on the extreme left is ~20 kb and not shown to scale.

DETAILED DESCRIPTION OF THE
PREFERRED EMBODIMENTS

The present invention will be exemplified herein in terms of preferred embodiments for the isolation and use of DNA segments comprising sequences encoding the HA synthase gene from *Streptococcal* sources. However, it will be appreciated by those of skill in the art that in light of the present disclosure the invention is also applicable to the isolation and use of the HA synthase enzyme from virtually any source, such as *Streptococcus pyogenes, S. equisimilis,* other group A or group C streptococcal strains or eukaryotic sources such as dermal or synovial fibroblasts, chondrocytes, trabecular-meshwork cells or rooster comb mesodermal cells which contain HA synthase encoding DNA that is actively transcribed (and is a suitable source of mRNA for the preparation of cDNA libraries).

The preferred application of the present invention to the isolation and use of *streptococcal* HA synthase DNA involves generally the steps of (Sambrook, et al., 1989) isolation of *streptococcal* genomic DNA; preparation of a genomic DNA library, such as in a bacteriophage lambda; screening the library with oligonucleotides from the derived sequence; isolating clones and subclones of phage with the oligonucleotide; excising the resident plasmid from within the phage genome or ligating a purified DNA into a selected site in a cloning vector; (Trieu-Cuot, et al., 1991) transfection of host *Streptococcus* or *E. coli* cells with the recombined vector; and selection of colonies expressing HA synthase or HA itself through the application of specially designed screening protocols. Following identification of a clone which contains the HA synthase gene, one may desire to reengineer the HA synthase gene into a preferred host/vector/promoter system for enhanced production of HA.

A. Cloning of Hyaluronate Synthase Gene

To clone the HA synthase gene, hasA, the present inventors used transposon insertion mutagenesis to identify the locus that is responsible for capsular formation. Genomic DNA from a transposon-tagged mutant of the *Streptococcus pyogenes* strain S43 was isolated from bacteria following hyaluronidase treatment, chloroform/isoamyl extraction and ethanol precipitation. It is believed to be important to provide a DNA fragment encoding a full length or essentially full length enzyme because the initial screening protocol requires expression of a functional enzyme shown to synthesize HA.

The identification and verification of the HA synthase gene was accomplished by analyzing transposon-directed mutants and cells that have been transformed with the HA synthase gene of the present invention. The assay is based on the formation of a polysaccharide capsule in acapsular strains of *Streptococci* and heterologous bacteria. Initially TN916 insertional mutants were screened for an acapsular, non-mucoid phenotype. The ends of the transposon were then used to obtain sequence in the vicinity of the interrupted gene to direct the cloning of the wild-type hasA gene.

Figure 2:
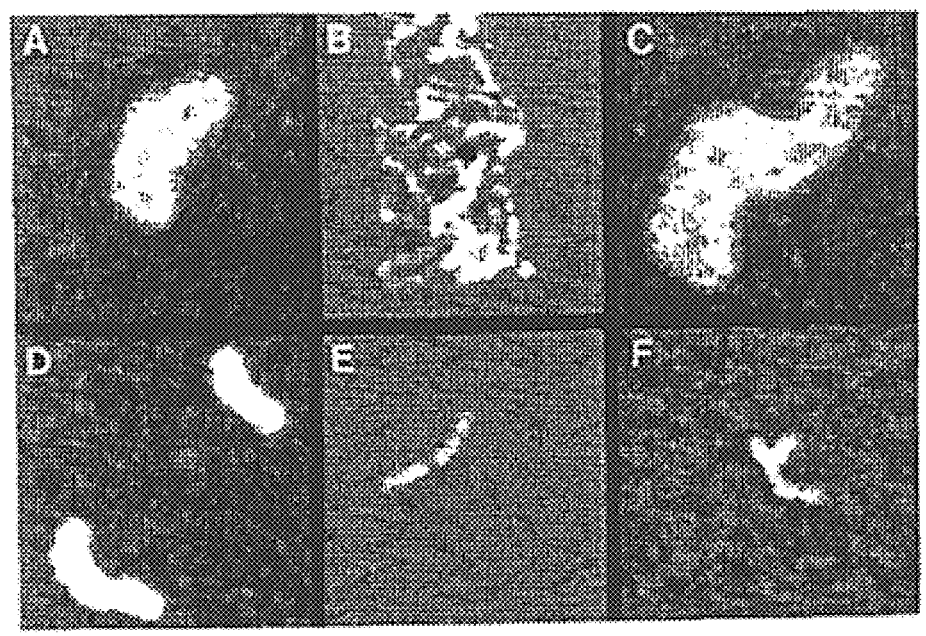
FIG. 2: Visualization of HA capsules in transformed bacteria by light microscopy. These photomicrographs of early log cultures stained with India ink (Collins and Lyne, 1976) were taken on a Leitz Laborux microscope at 1000× magnification. The results depict the ability of plasmids pPD41 or pPD41Δ5, but not pAT19 alone or pPD41Δ7, to direct HA capsule biosynthesis after transformation into the acapsular *S. pyogenes* mutant S43Tn7 or into normally acapsular *E. faecalis*. The bright halo surrounding the cells is the HA capsule. Ovine testicular hyaluronidase treatment destroyed the capsule. Panels: A, wild-type S43; B, S43Tn7 (pAT19); C, S43Tn7(pPD41); D, *E. faecalis*(pPD41Δ5); E, *E. faecalis*(pPD41Δ7); F, *E. faecalis* (pPD41Δ5) treated with 500 units/ml hyaluronidase (type V, 2000 u/mg) for 30 min at 37° C.

A contiguous three kilobase pair region of DNA (FIG. 1) was isolated from Group A *Streptococcus pyogenes* [GAS] that can direct hyaluronic acid [HA] capsule biosynthesis in acapsular mutants as well as heterologous bacteria (FIG. 2). The DNA was identified by transposon 916 insertional mutagenesis and subcloned into a plasmid shuttle vector. Mutant acapsular GAS or *Enterococcus faecalis* containing this plasmid, but not vector alone, displayed a mucoid phenotype on agar plates, possessed a capsule as seen by light microscopy, and produced HA in quantities comparable to wild-type GAS. The polysaccharide was shown to be authentic HA based on its recognition by a specific HA-binding proteoglycan and its degradation by *Streptomyces* hyaluronate lyase. *Escherichia coli* with the complementing plasmid also produced HA, but at only 10% of the level made by the above cells. *E. coli* minicell analysis showed that two proteins, 42 and 45 kDa, are expressed by the functional DNA insert. Deletion analysis of the insert in the minicells revealed that the 42 kDa protein is essential for HA production.

One may also desire to characterize the *streptococcal* or other HA synthases in terms of their kinetics and physical and chemical properties. The parameters, $K_m$ and $V_{max}$, are determined from a double reciprocal plot of the velocity of the reaction versus substrate concentration (Lineweaver-Burke plot). Properties which may be of interest may include the enzyme's thermostability, optimum pH for activity, effects of various ions, and effects of various inhibitors. Isoelectric focusing will be used to determine the isoelectric point of the synthase. Understanding these factors would provide basic information that may further allow one the ability to better determine what alterations in their primary sequence can provide additional advantages.

By appropriate modification of the DNA segment comprising the gene for HA synthase (e.g., deletion of membrane spanning domains of the protein), the enzyme can be converted to a form that may be secreted by the transfected bacterial host. This enzyme in soluble form, if still active in the ability to synthesize HA, would provide substantial improvement in the ease of purification of this modified enzyme and in its potential utility in an enzyme reactor system for the in vitro production of HA.

B. Typical Genetic Engineering Methods which May be Employed

If cells without formidable cell membrane barriers are used as host cells, transfection is carried out by the calcium phosphate precipitation method, well known to those of skill in the art (Sambrook, et al., 1989). However, other methods may also be used for introducing DNA into cells such as by nuclear injection, electroporation, protoplast fusion or by the Biolistic(tm) Bioparticle delivery System recently developed by DuPont (1989). The advantage of using this system is a high transformation efficiency. If prokaryotic cells or cells which contain substantial cell wall constructions are used, the preferred method of transfection is calcium treatment using calcium chloride (Sambrook, et al., 1989) or electroporation.

Construction of suitable vectors containing the desired coding and control sequences employ standard ligation techniques. Isolated plasmids or DNA fragments are cleaved, tailored, and relegated in the form desired to construct the plasmids required. Cleavage is performed by treating with restriction enzyme (or enzymes) in suitable buffer. In general, about 1 μg plasmid or DNA fragments are used with about 1 unit of enzyme in about 20 μl of buffer solution. (Appropriate buffers and substrate amounts for particular restriction enzymes are specified by the manufacturer.) Incubation times of about 1 hour at 37 degree(s) are workable.

After incubations, protein is removed by extraction with phenol and chloroform, and the nucleic acid is recovered from the aqueous fraction by precipitation with ethanol. If blunt ends are required, the preparation is treated for 15 minutes at 15 degree(s) C. with 10 units of Polymerase I (Klenow), phenol-chloroform extracted, and ethanol precipitated. For ligation approximately equimolar amounts of the desired components, suitably end tailored to provide correct matching are treated with about 10 units T4 DNA ligase per 0.5 μg DNA. When cleaved vectors are used as components, it may be useful to prevent relegation of the cleaved vector by pretreatment with bacterial alkaline phosphatase.

For analysis to confirm functional sequences in plasmids constructed, the ligation mixtures are used to transform *E. coli* K5 strain Bi8337-41 (Gupta, et al., 1982), and successful transformants selected by erythromycin resistance where appropriate. Plasmids from the library of transformants are then screened for bacterial colonies that exhibit HA production. These colonies are picked, amplified and the plasmids purified and analyzed by restriction mapping. The plasmids showing indications of a functional HA synthase gene are then further characterized by sequence analysis by the method of Sanger (Sanger, et al., 1977), Messing (Messing, et al., 1981), or by the method of Maxam (Maxam, et al., 1980).

C. Host Cell Cultures and Vectors

In general, prokaryotes are preferred for the initial cloning of DNA sequences and construction of the vectors useful in the invention. It is anticipated that the best host cells may be Gram-positive cells, particularly those derived from the group A and group C *Streptococcal* strains. Bacteria with a single membrane, but a thick cell wall such as *Staphylococci* and *Streptococci* are Gram-positive. Gram-negative bacteria such as *E. coli* contain two discrete membranes rather than one surrounding the cell. Gram-negative organisms tend to have thinner cell walls. The single membrane of the Gram-positive organisms is analogous to the inner plasma membrane of Gram-negative bacteria. The preferred host cells are *Streptococcus* strains that are mutated to become hyaluronidase negative or otherwise inhibited (EP144019, EP266578, EP244757). *Streptococcus* strains that have been particularly useful as suitable hosts include *S. pyogenes* S43, *S. equisimilis* and *S. zooepidemlcus*.

Although *E. coli* is Gram-negative it is, nonetheless, a useful host cell in many situations, as shown in Examples I and IV. *E. coli* SURE™ cells were chosen as the initial recipient strain for transformation and cloning of the HA synthase gene because this strain has proven to be very useful in recombinant DNA studies. It is a widely used host and is specifically engineered for recombinant DNA work. *E. coli* χ1448 was chosen for verification of HasA protein expression because of its utility as a minicell expression system. Other *E. coli* strains may also be useful for expression of the shuttle vectors pAT19 and pSA3 containing the HA synthase gene. For example, *E. coli* K12 strain 294 (ATCC No. 31446) may be useful. Other strains which may be used include *E. coli* B, and *E. coli* K5. These examples are, of course, intended to be illustrative rather than limiting.

Prokaryotes may also be used for expression. For the expression of HA synthase in a form most likely to accommodate high molecular weight HA synthesis, one may desire to employ *Streptococcus* species such as *S. equisimilis, S. pyogenes* or *S. zooepidemicus*. The aforementioned strains, as well as *E. coli* W3110 (F-, lambda-, prototrophic, ATCC No. 273325), bacilli such as *Bacillus subtilis*, or other enterobacteriaceae such as *Salmonella typhimurium* or *Serratia marcescens*, and various *Pseudomonas* species may also be used, as described in Example V.

In general, plasmid vectors containing origins of replication and control sequences which are derived-from species compatible with the host cell are used in connection with these hosts. The vector ordinarily carries an origin of replication, as well as marking sequences which are capable of providing phenotypic selection in transformed cells. For example, *E. coli* is typically transformed using pBR322, a plasmid derived from an *E. coli* species. pBR322 contains genes for ampicillin and tetracycline resistance and thus provides easy means for identifying transformed cells. A pBR plasmid or a pUC plasmid, or other microbial plasmid or phage must also contain, or be modified to contain, promoters which can be used by the microbial organism for expression of its own proteins.

Those promoters most commonly used in recombinant DNA construction include the lacZ promoter, tac promoter, the T7 bacteriophage promoter, β-lactamase (penicillinase) and tryptophan (trp) promoter system (Ausbel, et al., 1987). While these are the most commonly used, other microbial promoters have been discovered and utilized, and details concerning their nucleotide sequences have been published, enabling a skilled worker to ligate them functionally with plasmid vectors (Ausbel, et al., 1987). Also for use with the present invention one may utilize integration vectors.

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in *Saccharomyces*, the plasmid YRp7, for example, is commonly used (Ausbel, et al. 1987). This plasmid already contains the trpl gene which provides a selection marker for a mutant strain of yeast lacking the ability to grow without tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan. Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, cytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (Tissue Culture, 1973) has become a routine procedure in recent years (Sambrook, et al., 1989). Examples of such useful host cell lines are VERO and HeLa cells, Chinese hamster ovary (CHO) cell lines, and WI38, BHK, COS, and MDCK cell lines.

Other particularly useful host cell lines may be derived from dermal or synovial fibroblasts, mesodermal cells of rooster comb or the trabecular-meshwork cells of the eye. Expression vectors for such cells ordinarily include (if necessary) an origin of replication, a promoter located at the 5' end of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, bovine papilloma virus and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

Further, it is also possible, and often desirable, to utilize promoter or control sequences normally associated with the desired gene sequence, provided such control sequences are compatible with the host cell systems. An origin of replication may be provided either by construction of the vector to include an exogenous origin, such as may be derived from SV40 or other viral (e.g., Polyoma, Adeno, BPV) source, or may be provided by the host cell chromosomal replication mechanism. If the vector is integrated into the host cell chromosome, the latter mechanism is often sufficient.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Isolation of the HA Synthase Locus

Tn insertional mutagenesis was used to tag and to mutate capsule biosynthesis genes of GAS. The bacteriophage A25 transducing lysate from one acapsular mutant, designated S43Tn7 and containing two Tn916 elements, was found to transmit the nonmucoid phenotype to 3 out of 5 transductants. The two Tn elements were segregated by transduction; one Tn insertion characterized by higher MW HindIII fragments was found only in the nonmucoid transductants (S43Td7N), while the other Tn insertion event producing lower MW fragments was found only in the mucoid cells (S43Td7M). Nonmucoid transductants did not possess HA synthase activity or a capsule as determined by enzyme assays of membranes or by light microscopy, respectively.
Materials and Methods
Materials: Media reagents were from Difco. Restriction and DNA modifying enzymes were from Promega unless otherwise noted. Synthetic oligonucleotides were made at the UTMB Synthesis Facility or by Keystone Laboratories. All other reagents were of the highest grade available and from Sigma except where stated otherwise.
Strains and Vectors: $Escherichia\ coli$ was maintained on LB and grown in Superbroth with antibiotics for plasmid production. Other bacteria were grown as standing cultures on Todd-Hewitt broth supplemented with 1% yeast [THY] and horse serum (5–10%, Gibco). Cultures to be assayed for HA were grown using the dialyzate from dialyzed THY broth, (i.e. nutrients <10–14 kDa). The mucoid GAS strain, S43/192/4, was obtained from the Rockefeller Collection (Dochez, et al., 1919). Spontaneous strep$^r$ strains used as Tn acceptors were selected by plating ~$10^9$ cells on THY plates containing 1 mg/ml streptomycin and 3% defibrinated sheep blood (Colorado Serum). $Enterococcus\ faecalis$ CG110, a Tn916 donor (tetracycline resistant, 5 µg/ml), and pAM118, a plasmid with a Tn916 insert, were generously supplied by D. Clewell (Gawron-Burke and Clewell, 1984). The $E.\ coli$/Gram-positive shuttle vector pAT19 (erythromycin resistant, 8 µg/ml for Gram-positive or 150–200 µg/ml for $E.\ coli$) was provided by P. Courvalin (Trieu-Cuot, et al., 1991). The $E.\ faecalis$ host strain OG1RF was obtained from G. Dunny (Dunny, et al., 1991). $E.\ coli$ minicell strain χ1448 (Meagher, et al., 1977) was supplied by R. M. Macnab. The $E.\ coli$ hosts used were SURE, XL1-Blue (Stratagene), LE392, and KW251 (Promega).
DNA Purification and Sequencing: $Streptococcal$ chromosomal DNA was obtained by the method of Caparon and Scott (Caparon and Scott, 1991). $E.\ coli$ plasmid DNA was purified by the Instaprep method (5 Prime→3 Prime, Inc.) for screening or by the SDS/alkali method for cloning and blotting procedures (Sambrook, et al., 1989). Agarose (BioRad) gel-isolated DNA <7 kb was purified by GeneClean (Bio 101), while longer fragments were isolated using GlassMax cartridges (Gibco) to minimize shearing. λ DNA was prepared from phage purified on glycerol gradients (Sambrook, et al., 1989). Sequencing of double stranded plasmids was performed with Sequenase 2.0 (US Biochem) and α-[$^{35}$S]thiodATP (Amersham).
Lambda Library Production: The λZAPII library (Stratagene, 1–10 kb capacity) contained S43 wild-type DNA digested extensively with EcoRI. The λGEM system inserts (Promega, 9–23 kb capacity) consisted of S43 DNA partially digested with Sau3A. The λZAP system inserts from selected phage were excised and converted to plasmid form by coinfection with M13 helper phage (R408 or Exassist) according to Stratagene protocols.
Transposon Mutagenesis and Mutant Selection: The detailed methods for Tn mutagenesis, mutant selection, and the isolation and characterization of the Tn-tagged DNA are described in Example 3. Briefly, Tn insertional mutagenesis was done on a mucoid strep$^r$ S43 strain using the method of O'Connor and Cleary (O'Connor and Cleary, 1987). The nonmucoid mutant cells were enriched by Percoll step gradients in analogy to work done with Group B $Streptococci$ (Håkansson and Holm, 1986) after overnight outgrowth in double selective media as in Example III and FIG. 9. Candidate mutants of capsule biosynthesis were picked by visually screening for dry, discrete colonies versus wild-type wet, spreading colonies. The nonmucoid strains chosen for study did not: a) float in 50% Percoll, b) produce a capsule visualizable by India ink exclusion by light microscopy (Collins and Lyne, 1976), c) possess detectable HA synthase activity in membrane preparations, or d) synthesize extracellular HA as determined by a sensitive HA assay (see HA Polysaccharide Analysis). Transduction with the $streptococcal$ phage A25 (kindly supplied by M. Caparon) was used to determine the relevance of the various Tn916 insertions in the nonmucoid strains (Caparon and Scott, 1991).
Transposon Mapping and Isolation of the HA Synthesis Locus: An overview of the isolation procedures, as described herein below in Example 3, and as follows. After electrophoresis of chromosomal HindIII digests, the agarose gels (0.5–0.6%) were dried down directly (Ehtesham and Hasnain, 1991) and probed with the Tn916-containing EcoRI fragment of pAM118 labeled by the random primer method (Sambrook, et al., 1989). It was noted that one of the Tn916/S43 chimeric DNA fragments consistently migrated slower than the other fragments in HindIII digests of wild-type DNA. This chimeric fragment from preparative digests (5–15 µg) was isolated from an agarose gel with GlassMax and used as a DNA sequencing template to determine the sequence of the junction at the site of insertion; the DNA was not cloned first. A synthetic oligonucleotide derived from the termini of the right HindIII fragment of Tn916 (Clewell, et al., 1988) that reads outward from the Tn (AAAGTGTGATAAGTCC)(SEQ ID NO:4) was employed as a primer in a modification of the Sequenase method (US Biochem) for plasmids. The intact wild-type DNA was then obtained by screening the lambda libraries in the typical fashion (Sambrook, et al., 1989) with end-labeled oligonucleotide (TGGCACAATATGTCAGCCC)(SEQ ID NO:5) derived from the chromosomal sequence determined as above.

The HA biosynthesis locus is very unstable with respect to DNA deletion. The present inventors found that this characteristic made the subcloning difficult. The inventors found that three factors were essential in order to obtain stable clones of the hasA locus in its entirety: (1) use of a recombination deficient host (e.g. E. coli SURE™ cells), (2) use of the electroporation method of transformation and, (3) performing the recovery and all further growth of the recombinant cells at 30°–32° C. If these conditions were not followed for the subcloning of the hasA DNA, the vast majority of the target insert DNA was lost. Additionally, during the routine subculture of pPD41Δ5 at 37° C., the inventors have noted that deleted plasmids arose at a high rate. Therefore, a temperature of about 30° C. was used for any applications in which hasA and plasmid integrity was concerned.

To create a deletion set, the pPD41 plasmid linearized with XbaI and SphI was truncated by limited Exonuclease III digestion and Mung Bean nuclease treatment according to the Stratagene kit. The ligation mixtures were transformed into Epicurean SURE cells (Stratagene) and screened for insert size. E. coli was also transformed by the $Ca^{2+}$ method (Sambrook, et al., 1989).

Results

The gel-purified, Tn-tagged chromosomal DNA from S43Tn7 was used directly as a template in sequencing reactions with a Tn-specific primer that reads outward from the Tn terminus and into the insertion site. An oligonucleotide probe corresponding to a portion of the sequence of the interrupted DNA associated with the nonmucoid phenotype was then used as a hybridization probe for screening wild-type S43 genomic DNA libraries in λ phage. An excised λZAP clone, designated pB3, containing a 5.5 kb EcoRI fragment was obtained (FIG. 1). However, differences between the wild-type and Tn-mutant genomes were noted by Southern analysis. Since previous studies showed that Tn916 can cause deletions of chromosomal DNA (Dougherty and van de Rijn, 1992), the inventors then determined that at least 4 kb of DNA flanking the small arm (5 kb HindIII portion of Tn) was missing in S43Tn7 and S43Td7N (FIG. 1). Therefore, a larger wild-type genomic fragment spanning the deletion was obtained from the λGEM library. A 6.6 kb portion of DNA adjacent to pB3 was subcloned into pAT19 and designated pPD41 (FIG. 1).

The various plasmids were introduced into acapsular Streptococcus mutants as well as into heterologous bacteria. Table II shows HA produced by cultures (pooled spent media plus SDS cell extract) grown in dTHY. HA was determined by the HA TEST assay kit (Pharmacia, Uppsala, Sweden). The HA concentration was normalized per $A_{600}$ unit of cells. The pPD41 plasmid confers the ability to synthesize HA in the three species tested (DeAngelis, et al., 1993a). The truncated version, pPD41Δ5, was the minimal size functional plasmid obtained.

TABLE II

HA production by various constructs.

| BACTERIAL STRAIN | PLASMID | HA ng/μl |
|---|---|---|
| dTHY media alone | — | 1[a] |
| S. pyogenes | | |
| S43 | — | 1120 |
| S43Tn7 | pAT19 | 8 |
| S43Tn7 | pPD41 | 640 |
| S43Tn11[b] | pAT19 | 3 |
| S43Tn11 | pPD41 | 860 |
| S43Tn11 | pB3 | 6 |
| E. faecalis OG1RF | pAT19 | 2 |
| | pPD41 | 690 |
| E. coli SURE | pPD41 | 60 |
| | pPD41Δ4 | 80 |
| | pPD41Δ5 | 80 |
| | pPD41Δ6 | 2 |

[a]The media alone contains about 1 ng/μl HA after dialysis. The apparent "background" is reported for each host.
[b]S43Tn11 is an acapsular, HA synthase negative, Tn-containing strain that was shown by transduction analysis to be a spontaneous mutant.

EXAMPLE II

Characterization of the HA Synthase Locus

When pPD41 was electroporated into the original acapsular Tn mutant, S43Tn7, or a spontaneously arising nonmucoid strain, S43Tn11, transformant colonies displayed the mucoid phenotype on agar plates, while cells with pB3 or pAT19 were nonmucoid. The capsules of the complemented cells were easily visualized by microscopy with India ink and were indistinguishable from the wild-type (FIG. 2). Ovine testicular hyaluronidase treatment of the cultures completely destroyed these capsules.

Using a sensitive radiometric assay, HA was detected in the cultures of the Tn-mutants containing pPD41 in amounts comparable to the wild-type parent (as shown in Table II). Transformants with pB3 or pAT19, as well as the original mutant without plasmid, did not produce HA (Table II). The HA was detected by proteoglycan binding; this high affinity interaction is very specific and is widely accepted as evidence for the presence of HA (Tengblad, 1980). As in the case of the GAS mutants, E. faecalis or E. coli containing pPD41 produced HA (Table 1). By microscopy with India ink, E. faecalis, but not E. coli containing pPD41 possessed a substantial capsule.

Materials and Methods

HA Synthase Preparation and Assay: HA synthase was obtained from membranes of late log phase cells disrupted by sonication in PBS (20% cell suspension, dry ice/50% methanol bath, 4×2 min, Heat Systems W-380 with microprobe). Debris was removed by centrifugation at 12,000 g×10 min at 4° C., and then the membrane fraction was harvested from the supernatant by ultracentrifugation (100,000 g×60 min). The membranes (5–300 μg protein) were incubated with UDP-[$^{14}$C]GlcUA (250 mCi/mMole, ICN) in the assay as described by Triscott and van de Rijn (Triscott and van de Rijn, 1986). Specificity of polymerization was tested by omitting UDP-GlcNAc. Incorporation of the radiolabel into high MW polymers was measured by paper chromatography (Prehm, 1983).

HA Polysaccharide Analysis: The presence of HA in bacterial cultures (early log for S43 derivatives, late log for all others) was determined using the HA TEST radiometric assay (range 5–500 ng, Pharmacia). The detection is based on inhibition of $^{125}$I-proteoglycan binding to HA immobilized on beads by soluble HA in the sample. Secreted or released HA in cultures grown on dTHY was measured by assay of the supernatant fraction after centrifugation (11,000 g×5 min). Cell-associated HA was determined by extracting the cell pellet in 1/10 vol of PBS containing 0.01 SDS for 40 min at 37° C. The cells were then removed by centrifugation as above. The final SDS concentration in the HA assay never exceeded 0.001%.

HA was also purified by cetyltrimethylammonium bromide (CTAB) precipitation. The pooled media supernatant and cell extracts (treated with 0.1 mg/ml trypsin for 40 min at 37° C. followed by SDS extraction as above) from 25 ml cultures were adjusted to 0.3% CTAB and allowed to stand at 37° C. for 15 min. The precipitate was collected by centrifugation (3,000 g×20 min at room temperature) and resuspended in 0.7 ml of 2 M NaCl with gentle mixing for 40 min. The solubilized fraction (clarified by high speed centrifugation, 11,000 g×5 min) was then precipitated by addition of 2 volumes of ethanol. After 5 min, the solids were collected by high speed centrifugation. The pellet was washed with 70% ethanol/30% 2 M NaCl and then 70% ethanol. After brief drying, the pellet was resuspended in 2 M NaCl and ethanol precipitation was repeated as above. The final pellet was dissolved in 0.2 ml water overnight with gentle mixing at 4° C.

The uronic acid content of the purified material was measured by the carbazole assay with glucuronic acid as standard (Bitter and Muir, 1962). The MW of the polymers and authentic rooster comb HA standards (Lifecore) were compared by polyacrylamide gel electrophoresis (PAGE) (Min and Cowman, 1986) and size exclusion chromatography. To verify the nature of the polysaccharide, samples were digested with hyaluronate lyase from *Streptomyces hyaluroniticus* in 50 mM sodium acetate, pH 5.3, at 42° C. before analysis. Sepharose 4B (Pharmacia, 1×25 cm column, 20 ml bed volume) eluted with PBS was used to fractionate the various polymers. The column fractions were assayed by the carbazole method and the HA TEST kit was used to confirm the major peak identity. The column was calibrated with dextrans ($2\times10^6$, $5\times10^5$, $4\times10^4$ Da; Pharmacia) and lactose as well as the HA standards.

Minicell Analysis: The identity of plasmid-encoded polypeptides was determined by radiolabeling proteins produced in minicells (Matsumura, et al., 1977). Minicells from *E. coli* χ1448 containing pAT19, pPD41Δ5, or pPD41Δ7 were harvested from sucrose gradients and washed with PBS containing 0.01% gelatin. The minicells were incubated at 37° C. for 1 hr in minimal salts with glycerol and all amino acids except Met and Cys. The minicells were then labeled with $^{35}$S-Translabel (ICN) for 30 min at 37° C. followed by a 5 min Met/Cys chase. The minicells were then washed with PBS and analyzed by SDS-PAGE after boiling (3 min) in Laemmli sample buffer (Laemmli, 1970). The gels were stained with Coomassie Blue, dried, and exposed to XAR-5 film (Kodak).

Miscellaneous: Of several published electroporation methods for use with Gram-positive bacteria, the present inventors found that only the technique of Caparon and Scott (Caparon and Scott, 1991) was successful in transforming S43 derivatives with plasmids (0.5 to 20 transformants/µg DNA).

Results

To determine the minimum size of the locus directing HA biosynthesis, the complementing DNA insert of pPD41 was reduced by limited exonuclease digestion of the plasmid from the SacI end of the pAT19 multiple cloning site. *E. coli* transformed with plasmids containing an insert of ~3 kb (e.g. 5 min deletion, pPD41Δ5; see FIG. 1) still produced HA, while cells with smaller inserts (e.g. 6 min deletion, pPD41Δ6, ~2.3 kb or 7 min deletion, pPD41Δ7, ~1.7 kb) did not make HA (Table II). The *E. faecalis* cells transformed with pPD14Δ5 produced hyaluronidase-sensitive capsules as assessed by microscopy (FIGS. 2D & 2F), and formed mucoid colonies on agar plates, whereas the cells containing pPD41Δ7 were equivalent to untransformed *E. faecalis* (FIG. 2E). *E. faecalis* has not been reported to produce a capsule or any exopolysaccharides. Therefore, the pPD41Δ5 insert is responsible for HA capsule biosynthesis.

Figure 3:
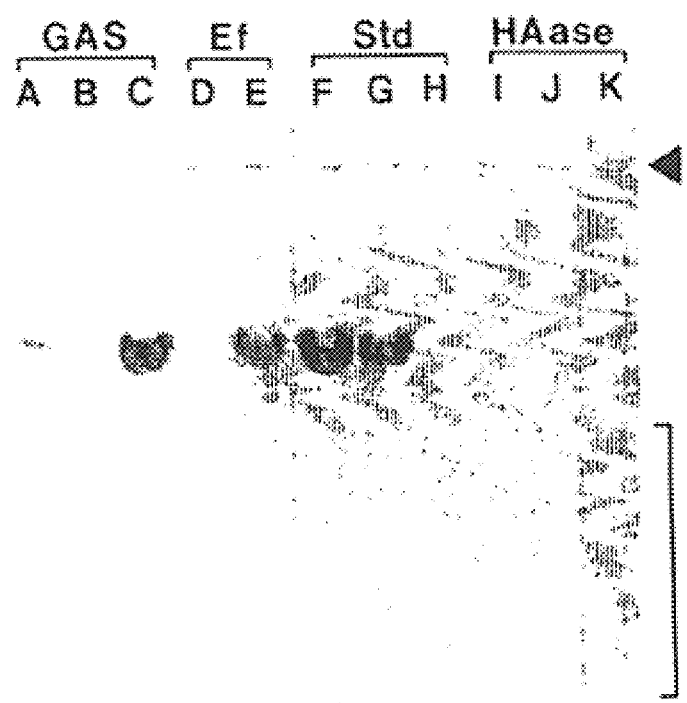
FIG. 3: PAGE analysis of polysaccharides produced by various transformed bacteria. Authentic HA (std) and polysaccharides purified from cell cultures as described by DeAngelis, et al. (1993a) were electrophoresed on a 4% gel and stained with Alcian Blue. Strains without pPD41 or pPD41Δ5 do not produce HA. The majority of the polymer population in each sample migrated similarly to high MW HA (lanes F,G). The bracket on the right marks the extent of staining of the low MW HA standard, which did not photograph well (lane H). The arrowhead indicates the top of the gel. *Streptomyces* hyaluronate lyase [HAase] treatment (20 units, 15 min) completely degraded the bacterial products. One μg (by carbazole assay) samples were loaded in lanes A-H and 8 μg samples were loaded in I-K. Lanes: A, S43; B, S43Tn7 (pAT19); C, S4 3Tn7 (pPD41); D, *E. faecalis* (pPD41Δ7) ; E, *E. faecalis* (pPD41Δ5); F, native HA, viscosity=13,172; G, HA with viscosity=1,589; H, HA with viscosity=20; I, HAase-treated sample C; J, HAase-treated sample E; K, HAase-treated sample F.

The extracellular polysaccharides produced by the various bacteria containing the pPD41 family of plasmids were further characterized by gel filtration chromatography and PAGE. All polysaccharides possessed $M_r$s on the order of $10^6$, since they eluted in the void volume and the first included fractions on the Sepharose 4B column, well before a 500 kDa dextran standard (not shown). By electrophoretic analysis, wild-type S43 HA and polysaccharide from mutant GAS strains with pPD41 or *E. faecalis* with pPD41Δ5 migrated similarly compared to authentic high MW HA standards (FIG. 3). The specific *Streptomyces* hyaluronate lyase degraded both authentic HA and the polysaccharides produced by S43Tn7 or *E. faecalis* containing the complementing plasmids (FIG. 3).

Figure 4:
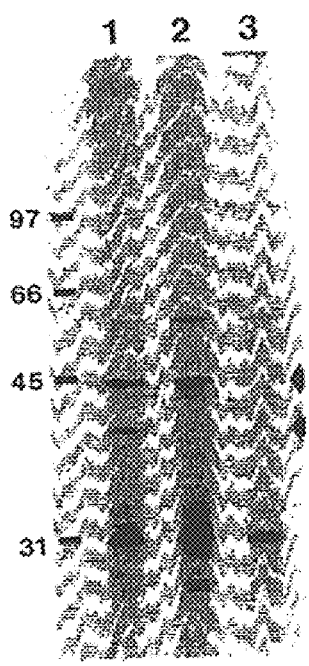
FIG. 4: SDS-PAGE analysis of proteins synthesized by pPD41 deletion plasmids in *E. coli* minicells. Minicells labeled with [$^{35}$S]Met/Cys were lysed by boiling in SDS-sample buffer and electrophoresed on a 10% gel. Cells containing the pPD41Δ5 plasmid produce HA and two proteins are seen on this autoradiogram (24 hr exposure) at 42 and 45 kDa (lane 1, positions marked with arrows) that are not produced by vector alone (lane 3). Cells containing the pPD41Δ7 plasmid do not produce HA and only synthesize the 45 kDa protein (lane 2). Standards (BioRad, low MW) are shown in kDa.

The *E. coli* minicell system provides a convenient way to determine the number and size of proteins encoded by genes on episomal plasmids (Meagher, et al., 1977; Matsumura, et al., 1977). Minicell analysis revealed that at least two proteins were encoded on the complementing DNA that directed HA capsule biosynthesis (FIG. 4). In addition to vector-derived proteins, the nonfunctional pPD41Δ7 encoded a prominent 45-kDa protein. Minicells with the HA-producing pPD41Δ5 plasmid produced a 42-kDa protein as well as the 45-kDa species, indicating that the former protein is essential for HA synthesis. The present inventors calculate that about 80% of the coding capacity of the ~3 kb insert in pPD41Δ5 is utilized for these two proteins.

Neither the purification nor the cloning of the HA synthase has been successfully demonstrated in either bacteria or eukaryotes. Prehm and Mausolf (Prehm and Mausolf, 1986) implicated a 52-kDa protein from GCS as the HA synthase by affinity labeling with periodate-oxidized sugar nucleotides. A polyclonal antibody to this protein inhibited HA synthase activity of membranes (Prehm and Mausolf, 1986). However, the active HA synthase was not purified. The gene corresponding to the 52 kDa protein was then cloned using the antibody and, although the assertion of cloning the HA synthase gene was made, the present inventors have found this conclusion to be invalid; the deduced sequence had similarities to an oligopeptide transport protein of *Bacillus subtilis* (Lansing, et al., 1993). van de Rijn and Drake (van de Rijn and Drake, 1992) found three polypeptides (42, 33, and 27 kDa) from GAS and GCS membranes that were photoaffinity labeled by a substrate analogue, azido UDP-glucuronic acid. Excess UDP-GlcA inhibited incorporation of the analogue but labeling of all three polypeptides was stimulated upon addition of the other precursor of HA, UDP-GlcNAc (van de Rijn and Drake, 1992). The 42 kDa protein labeled in the pPD41Δ5-containing minicells is the same size as one of the proteins photoaffinity labeled with a substrate analog (van de Rijn and Drake, 1992). However, the proteins of 32 and 27 kDa that were also labeled were not observed in the inventors studies. Dougherty and van de Rijn (Dougherty and van de Rijn, 1992) used Tn insertional mutagenesis to identify a GAS genetic locus associated with HA synthase activity.

Two open reading frames were described schematically but no sequence information was reported and no in vivo or in vitro HA synthase activity was reported.

None of the above studies functionally reconstituted HA synthesis in an acapsular mutant or in heterologous bacteria with cloned *streptococcal* DNA. The results of the inventors, however, show that a contiguous 3 kb region of the GAS chromosome, encoding proteins of 42 and 45 kDa, can direct HA biosynthesis in GAS mutants as well as in *E. faecalis* and Gram-negative *E. coli*.

EXAMPLE III

Cloning of the HA Synthase Gene

Figure 5:
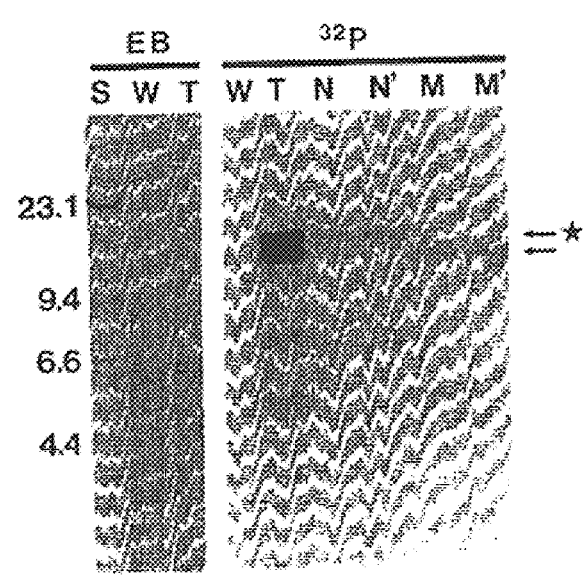
FIG. 5: Tn Mapping Analysis of Mutant and Transductant Strains. Southern analysis of HindIII digests of chromosomal DNA of various S43 strains using a Tn-specific probe ($^{32}$P panel, 48 hr autoradiogram) reveals that S43Tn7 (T) contains two Tn insertions (each Tn yields two bands due to an internal HindIII site). Transduction segregates the two Tns and produces nonmucoid (N,N') or mucoid (M,M') colonies (two independent clones of each are shown). Wild-type S43 (W) DNA does not hybridize with the probe. All the wild-type HindIII fragments detected with ethidium bromide (EB panel) migrate as ≦10 kb (S; λ HindIII standards in kb). Therefore, the chimeric Tn-tagged fragments (marked with arrows) were purified and sequenced directly. An oligonucleotide probe specific for the HA biosynthetic locus was derived from the fragment marked with the star.

The HA synthase gene of GAS was initially identified by Tn insertional mutagenesis as described in Example I. The bacteriophage A25 transducing lysate (Caparon and Scott, 1991) from one acapsular mutant (designated S43Tn7), which contained two Tn elements, transmitted the nonmucoid phenotype to 3 out of 5 transductants (FIG. 5). The nonmucoid transductants did not possess HA synthase activity or a capsule by light microscopy, but the mucoid transductants were equivalent to wild-type S43. HindIII digests of mutant S43Tn7 chromosomal DNA showed two bands migrating at 16 and 18 kb on agarose gels that corresponded to the higher MW bands detected by a Tn-specific probe on Southern blots of all TN916 mutants (FIG. 5). These larger species are the result of adding 10 kb of Tn DNA to the S43 HindIII fragment at the insertion site.

Since the Tn-tagged DNA from S43Tn7 was well resolved from the other HindIII fragments, it could be gel-purified. The 18 kb chimeric fragment associated with the HA biosynthesis defect was therefore used directly as a template for sequencing reactions with a Tn-specific primer that reads outward from the Tn terminus and into the interrupted gene. An oligonucleotide (SEQ ID NO:5), corresponding to a portion of the sequence of the interrupted gene from the 18 kb chimeric fragment, was used as a hybridization probe for screening wild-type S43 genomic DNA libraries in λphage.

An excised λZAP clone, pB3, containing a 5.5 kb EcoRI fragment was selected and studied further. However, Southern analysis utilizing various oligonucleotide probes to the sequence of pB3 revealed some discrepancies between the wild-type and Tn-mutant genomes (e.g. the SEQ ID NO:6 oligo hybridized to S43 but not S43Tn7, while the SEQ ID NO: 5 oligo hybridized to both) Therefore, a larger genomic fragment spanning the Tn-induced deletion (DeAngelis, et al., 1993a,b) was obtained from the λGEM library. After an extensive subcloning effort and subsequent exonuclease III deletion, a 3.2 kb fragment of S43 DNA was identified as a locus that could direct HA biosynthesis (DeAngelis, et al., 1993a).

Materials and Methods

Materials and Strains: Restriction and DNA modifying enzymes were from Promega unless otherwise noted. All other reagents were of the highest grade available from Sigma unless stated otherwise. Media reagents were from Difco. Cultures to be assayed for HA were grown using the dialysate from dialyzed THY broth (i.e. nutrients <10–14 kDa). The mucoid GAS strain, S43/192/4, was obtained from the Rockefeller Collection (Dochez, et al., 1919). *E. coli* K5 (Bi8337-41) was obtained from I. and F. Orskov (Copenhagen, Denmark; Gupta, et al., 1982). All other strains and plasmids used were described by DeAngelis, et al., (1993a).

Tn Mutagenesis and Mutant Selection: Tn insertional mutagenesis was conducted by the method of O'Connor and Cleary (O'Connor and Cleary, 1987) except that ovine hyaluronidase (Type V) was added to the GAS culture (0.2 mg/ml, 1 hr at 37° C.) after overnight growth and used at a higher concentration (0.1 mg/ml) in the mating plate media. The Tn916 donor, *Enterococcus faecalis* CG110 (Gawron-Burke and Clewell, 1984), was mated on nitrocellulose filters (88 mm, 0.45 μm, Micron Separation, Inc.) with strep$^r$ S43. The mating mixture was scraped off the filters with 0.4 ml THY containing 1 mg/ml streptomycin and 5 μg/ml tetracycline.

Figure 9:
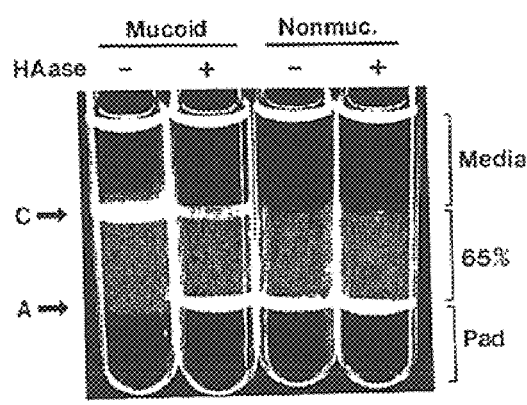
FIG. 9: Buoyant density separation of acapsular and encapsulated *streptococci*. The procedure described herein in Example III was used in this example to distinguish encapsulated, mucoid S43 cells and acapsular, nonmucoid NZ131 cells except that, for purposes of illustration, the 65% Percoll layer was underlaid with a 100% Percoll pad. Note that cells with a capsule (C) are at the top interface while the acapsular or enzyme-treated cells (A) appear at the lower interface (these cells would be in a pellet if not for the 100% Percoll pad). Hyaluronidase (HAase) treatment of the culture of the mucoid strain removes the capsule and increases the density so that the majority of the cells appear in the pellet.

The nonmucoid mutant cells were then enriched over Percoll (Pharmacia) step gradients (DeAngelis, et al., 1993b; Håkansson and Holm, 1986) as illustrated in FIG. 9. This selection process allowed about a thousand-fold more bacteria to be more readily examined than if plating methods were used directly after the mating step. Acapsular (or hyaluronidase-treated) cells pellet through 50% Percoll, but mucoid cells float at the interface. After overnight outgrowth (50–70 μl mating mixture/5 ml double selective media with 5% serum in a 15 ml tube), the cultures were underlaid with 2 ml of 50% Percoll in water and centrifuged (3,000 g×10 min). The media, the cells at the interface, and most of the Percoll were removed by aspiration and the high density "cell pellet" fraction was then used to inoculate 5 ml of fresh double selective media. Two further rounds of outgrowth for 4–8 hrs ($A_{600}$=0.2–0.6) and gradient enrichment were performed. Portions of the final cell pellet were streaked on double selective plates containing 5% sheep blood and visually screened for candidate mutants of capsule biosynthesis: those with dry, discrete colonies versus wild-type wet, spreading colonies.

The mutants were streak-purified and verified to be similar to wild-type S43 with respect to vigor, β-hemolysis, DNase secretion (using DNA/methyl green agar), and production of Group A carbohydrate (Ventrescreen, Hycor). Thirteen strains did not have HA synthase activity, produce capsules or contain HA (DeAngelis, et al., 1993a) but only one strain, S43Tn7, transduced (Caparon and Scott, 1991) the nonmucoid phenotype.

Tn Mapping and Gene Isolation: Chromosomal DNA purified (Caparon and Scott, 1991) from the mutants and transductants was cut with HindIII and analyzed by Southern hybridization. After electrophoresis, the agarose gels were dried down directly (Ehtesham and Hasnain, 1991) and probed with the Tn-containing EcoRI fragment of pAM118 (Gawron-Burke and Clewell, 1984) labeled by random priming (New England Biolab kit). The hybridization was conducted overnight at 65° C. in 1×HPB (0.5 M NaCl, 5 mM EDTA, 0.1 M $Na_2PO_4$, pH 7.2) containing 1% sarcosyl, and the gel was then washed for 40 min with 20 mM Tris HCl, pH 8 at 22° C.

The 16 or 18 kb chimeric Tn-tagged fragments from preparative digests (5–15 μg) of S43Tn7 were isolated from gel slices using GlassMAX (Life Technologies) according to the manufacturer's instructions except that the DNA was eluted from the GlassMAX unit with 3 sequential additions of water at 65° C. The Sequenase method (USBiochem) for plasmids, with modifications noted below, was employed to sequence the junction at the site of Tn insertion directly from chromosomal DNA. A synthetic oligonucleotide (AAAGTGTGATAAGTCC)(SEQID NO:4) based on the termini of the right arm of TN916 that reads outward into the interrupted gene was used as the primer (Clewell, et al., 1988).

The purified DNA fragment (50–100 ng) was denatured with NaOH, neutralized with sodium acetate, and quickly ethanol precipitated in the presence of 10 μg of phenol/

CH₃Cl extracted glycogen. The primer SEQ ID NO:4 (0.22 pmol) was annealed to the template by slow cooling from 65° to 30° C. The labeling phase of the reaction was done with $Mn^{2+}$ buffer, 1:15 diluted labeling mix, and α[$^{35}$S] thiodATP (Amersham, 3,000 Ci/mMol) for 2 min at 20° C. The termination phase was done for 5 min at 37° C. with extension mix in the A and T reactions (0.6 μl) due to the A/T-rich nature of *streptococcal* DNA. Gels were electrophoresed, processed (Sambrook, et al., 1989), and exposed to XAR-5 film for 1–10 days at room temperature. Typically, the sequence of the Tn terminus/junction (6–10 bp) and 20–40 bases of the adjacent tagged *streptococcal* DNA were obtained.

The oligonucleotide derived from the chromosomal sequence determined above was used to screen two lambda libraries (DeAngelis, et al., 1993a,b) to obtain the intact wild-type DNA, in which the Tn insertion had occurred in the mutant. The phage were adsorbed onto nitrocellulose filters and processed in the typical fashion (Sambrook et al., 1989). The filters were hybridized with end-labeled oligonucleotide 5'-TGGCACAATATGTCAGCCC-3' (SEQ ID NO:5), in 1.8×HPB (1 pmol probe/8 ml) with 1% sarcosyl, 0.5% nonfat milk at 42° C. for 3 hr and washed with 0.5×HPB at the same temperature for 1 hr. The plaques yielding the strongest signal were replated and rescreened twice. Purified phage from a λZAP library were converted to plasmid form by coinfection of SURE or SOLR cells (Stratagene) with the Exassist helper phage (Stratagene). One clone, pB3, was analyzed by sequencing with Sequenase using the standard protocols. The phage selected from the λGEM library using SEQ ID NO:5 were screened with another oligonucleotide (5'-TATGGCTTAGTGCCATTCG-3') (SEQ ID NO:6), corresponding to the sequence found near the end of the pB3 insert, in order to obtain DNA adjacent to pB3.

Two positively hybridizing λGEM isolates, which formed small plaques and grew poorly in liquid lysates, were obtained. Large scale plate lysates with top and bottom agarose were needed in order to prepare their DNA (Sambrook, et al., 1989). The two clones (λ1X and λ2Y with 20 and 12 kb inserts, respectively) contained the same region of DNA as determined by direct sequencing of the λ DNA insert using the Circumvent method (New England Biolabs) and end-labeled oligonucleotide SEQ ID NO:6. The sequence obtained beyond the EcoRI site of pB3 (left site; DeAngelis, et al., 1993a) was used to make another oligonucleotide (5'-CAATCATACCACCAACTGC-3') (SEQ ID NO:7), for mapping analysis of the λ clones treated with various restriction enzymes.

Southern blot analysis showed that a fragment of about 7 kb could be excised from the smaller λ2Y clone using the EcoRI site in the S43 DNA and the SacI site of the λ vector. A portion of the digest was purified with a Magic minicolumn (Promega) and the fragments were ligated to pAT19 shuttle vector (Trieu-Cuot, et al., 1991) digested with EcoRI and SstI (Life Technologies). Attempts to subclone the *streptococcal* fragment in its entirety were thwarted by spontaneous deletions upon transformation into *E. coli* JM109. After using Epicurean competent SURE cells (Stratagene), using 32° C. for transformation recovery and all further growth, and restriction mapping ~70 recombinant colonies, a clone containing a 6.6 kb insert, designated pPD41, was obtained that could complement the HA biosynthesis defect of mutant GAS (DeAngelis, et al., 1993a).

Results
Isolation of Mutants

The inventors have used the difference in relative buoyant density to isolate acapsular mutants from a mating mixture of *Streptococcus pyogenes* strain S43 and an *Enterococcus faecalis* transposon TN916 donor (DeAngelis et al., 1993b). After centrifugation over a simple Percoll step gradient (50% pads), the cell pellet was harvested and used as a culture inoculum. Repeated cycles of growth and separation on Percoll gradients were performed to enrich for acapsular mutants in order to avoid painstakingly screening hundreds of plates inoculated with unselected cultures. The initial cell "pellet" may not be visible, but if it is processed for 3 additional cycles (after aspiration of the supernatant) even spontaneous acapsular mutants that occur at low frequency are obtained. Conversely, mucoid varieties can be enriched from mixtures of both cell-types or spontaneous revertants of nonmucoid mutants can be recovered; in this case the interface is harvested with a pipette and repeatedly processed as above. Isolation of either phenotype is finally accomplished by streaking out on agar plates. Quantitation of the capsular and acapsular phenotypes in a population of bacteria may be obtained by measuring the ratio of relative $A_{600}$ of resuspended cells harvested from both locations in the step gradient. This method is broadly applicable to other encapsulated microorganisms besides Group A *Streptococci* (e.g. Group C; unpublished observation) but optimization of the Percoll concentration and capsule degrading reaction conditions may be necessary.

The utility and optimization of the buoyant density centrifugation technique was also studied with various encapsulated and acapsular strains. The inventors have determined optimal concentrations of Percoll for separating encapsulated cells and acapsular cells by first using discontinuous step gradients of Percoll (e.g. 50%, 63%, 75%, 87%). Wild-type S43 cells were found at the 50%/medium interface. Hyaluronidase-treated wild-type S43 cells collected at the 63%/75% Percoll interface near the green marker beads (DMB-7, 1.10 mg/ml). This density value was close to the measured value reported as the "typical" bacterial cell density (1.08 mg/ml) in a recent survey (Guerrero, et al., 1985). Light microscopy with India ink (Collins and Lyne, 1976) was used to examine bacteria at both positions after centrifugation; all the cells at the medium/50% interface possessed capsules, while the cells with the highest density at the 63%/75% interface had no detectable capsule.

For bacteria with smaller capsules than the highly mucoid S43 strain, a simple 65% Percoll pad could distinguish capsule phenotypes among an array of Group A *streptococci* strains. Nonencapsulated cells were found in the pellet, while encapsulated cells appeared at the interface between the yellow media and clear Percoll (FIG. 9). The inventors determined the presence or absence of HA on the various strains by using a sensitive radiometric assay with a detection limit of 0.4 μg/ml of culture media. If the bacteria made at least 7 μg of HA per ml of cells per 1 $A_{600}$ unit, they were found at the interface of the Percoll layer and media. One strain, DW 1009, that produced 4 μg of HA per ml of cells, however, appeared in the pellet and, therefore, appears to be below the limit of detection by our simple and rapid centrifugation method. This strain, however, showed nonmucoid colony morphology and no evidence of a capsule by light microscopy. Hyaluronidase-treatment of the cultures of mucoid strains before centrifugation caused the vast majority of cells to pellet (FIG. 9), although some small clumps of cells may remain at the medium/Percoll interface due to incomplete digestion of their capsule.

The density separation method is surprisingly sensitive to the bacterial HA level. Strain NSA156 produced 7 μg/ml HA and floated on 65% Percoll. This strain, which produces only about 0.5% to 4% of the HA made by most encapsulated strains, does not appear mucoid on plates and its capsule was not visible with the light microscope. A further asset of the present method is that very small amounts of cells are readily visible; cells at the 65% Percoll/media interface, when viewed at an angle, cloud the junction's usual "mirror-like" appearance, while higher density cells are concentrated by the conical bottom of the centrifuge tube. Another benefit of this method is that it circumvents the need for fresh (<2 month old) radiometric assay kits for detection of hyaluronic acid and, therefore, such kits do not need to be continuously available in the laboratory. If further quantitation is needed on selected strains, these can also be stored and tested at a later date.

This density separation method is well suited for the sensitive determination of the presence of an HA capsule in clinical *streptococci* isolates; bacitracin-sensitive, β-hemolytic colonies from standard blood plates can be picked and assayed. In light of the capsule's importance as a virulence factor and the resurgence of *streptococcal* diseases in the USA and Europe, monitoring HA capsule production may be useful for tracking virulent strains or epidemiological trends. The only equipment needed is a 37° C. incubator or waterbath and a low-speed clinical centrifuge. In less than one day after the initial streak isolation on an agar plate, and with only a few minutes of hands-on labor, many isolates can be screened for capsule production. Inclusion of the hyaluronidase-treated control tube may not be necessary during routine screening, but rather can be used subsequently for verification of HA production.

hasA Cloning

Figure 8:
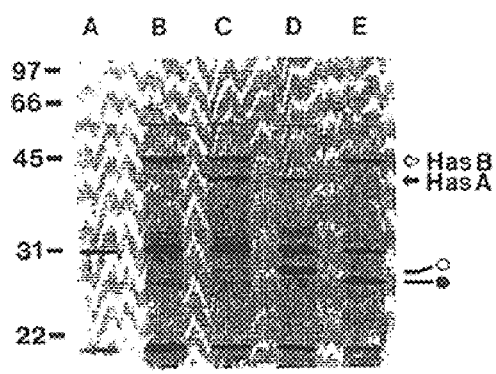
FIG. 8: *E. coli* Minicell Analysis of pPD41 Deletion Constructs. Minicells from χ1448 containing various plasmids were $^{35}$S-labeled and the proteins were separated on a 12.5% SDS-PAGE gel. This autoradiogram (10 hr exposure) shows that when hasA or hasB genes are disrupted, the predicted proteins (HasA, filled arrow at 42 kDa; HasB, open arrow at 45 kDa) are likewise affected. The truncated versions of HasA (filled circle) or HasB (open circle) are smaller as expected. Lanes: A, pAT19 vector, B, pPD41Δ7; C pPD41Δ5; D, pPDΔPstI; E, pPDΔEcoRV. Standards (BioRad, low MW) are marked in kDa.

The sequence of the complementing *streptococcal* DNA, the insert of pPD41Δ5, was obtained using both the nested nuclease deletion set with the M13 vector primers and the functional plasmid with custom oligonucleotides. Two major ORFs were present (FIG. 6) in agreement with the earlier minicell analysis (DeAngelis, et al., 1993a). The sequence of the first ORF, hasA, reveals the primary structure of a previously undescribed protein (FIG. 7)(DeAngelis, et al. (1993b) The deduced polypeptide contains 395 residues with a $M_r$=45,063 if the standard ATG initiation codon is used (or up to 419 residues if the alternate GTG initiation codon at position −72 is used). The 42-kDa protein observed by SDS-PAGE analysis of pPD41Δ5 minicells is assigned to be HasA because the pPD41Δ7 plasmid, missing about half of the hasA gene (FIG. 6), does not produce the 42 kDa species (FIG. 8). HasA is predicted (Kyte and Doolittle, 1982) to be an integral membrane protein due to at least four membrane-associated regions (3 predicted transmembrane segments) and to have a pI of 8.2.

EXAMPLE IV

Further Characterization of the hasA Gene

Figure 6:
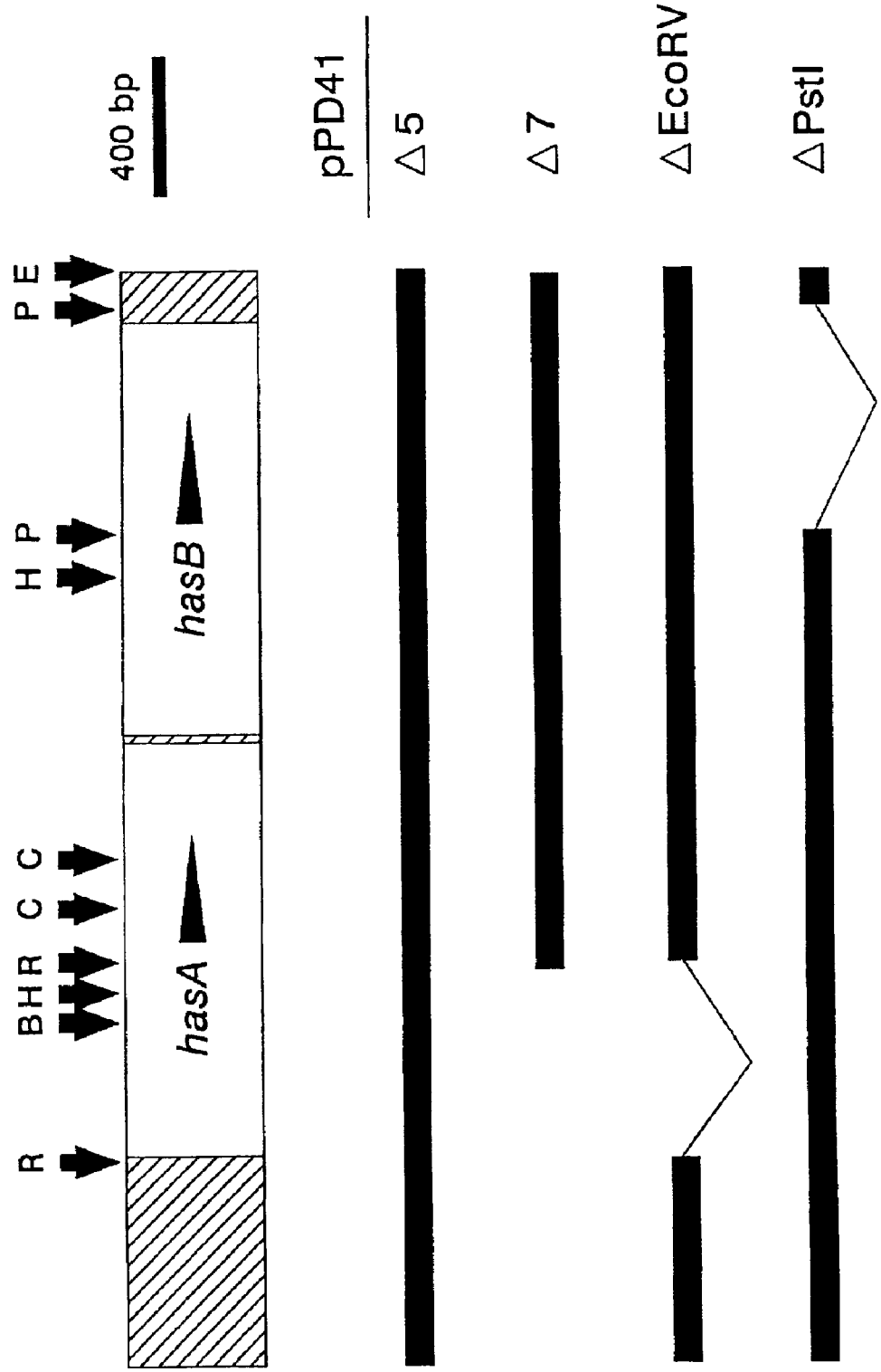
FIG. 6: Schematic Map of the HA Biosynthesis Locus and Various Plasmid Constructs. A restriction map of the complementing region of S43 DNA, containing two substantial ORFs, is shown. The hasA and hasB genes are translated in the same orientation but in different reading frames. In this schematic, the HasA open reading frame begins with the standard ATG codon. Sites for EcoRI (E), HindIII (H), ClaI (C), BglII (B), PstI (P), and EcoRV (R) are marked. The Tn insertion site was about 4 kb to the right of the E site on the wild-type map but the intervening chromosomal DNA was deleted in the S43Tn7 mutant (DeAngelis, et al., 1993). The various pPD41 deletion constructs are depicted (black lines) below the map. The cross-hatched areas represent flanking sequences on either side of the two open reading frames.

To identify the role of the two genes on the complementing *streptococcal* DNA, two constructs were made that substantially truncated either hasA or hasB (FIG. 6). One plasmid, pPDΔEcoRV, should produce the intact 45-kDa protein, HasB. The other, pPDΔPstI, should make the intact 42-kDa protein, HasA. The pPDΔEcoRV construct, in which the truncated HasA gene produced a new 27-kDa species (instead of the 42-kDa protein) as determined in minicells (FIG. 8), did not confer the ability to produce HA in any host (Table III).

Materials and Methods

Polypeptides encoded by plasmid genes were identified by $^{35}$S-labeling of proteins produced in minicells from *E. coli* χ1448 (Meagher, et al., 1977), containing pAT19 alone or various constructs containing S43 DNA, as described by DeAngelis (DeAngelis, et al., 1993a). DNA purification and sequencing, lambda library production, nested deletion set construction, and HA synthase preparation and assay were performed as described earlier (DeAngelis, et al., 1993a). Targeted internal deletions were made by digesting pPD41Δ5 DNA with either EcoRV or PstI, purifying the DNA with Magic minicolumns and recircularizing by ligation. The ligation mixtures were transformed into Electrocompetent SURE cells (Stratagene) and screened for insert size. HA was quantitated using the Pharmacia HA Test Kit (DeAngelis, et al., 1993a). UDP-Glc dehydrogenase activity was measured as described (Dougherty and van de Rijn, 1993) except cells (from 4.5 ml overnight cultures in dialyzed THY, washed and resuspended in 0.4 ml buffer) were disrupted by vortexing with an equal volume of washed glass beads (75–150 μm, 5×30 s at 4° C. with 30 s on ice between mixing). The extracts were assayed at 30° C. for a UDP-Glc-dependent increase in $A_{340}$ corresponding to NADH production. Protein was measured by the Bradford assay (Bradford, 1976) with a BSA standard.

Results

Minicells containing pPDΔPstI produced two nonvector-derived proteins, the intact 42-kDa protein and a 29-kDa truncated version of HasB (FIG. 8). The deleted hasB gene product is predicted to be 23-kDa based on the sequence. When transformed into SURE or χ1448 cells, pPDΔPstI could not direct HA synthesis (Table III). On the other hand, *E. coli* K5 transformed with pPDΔPstI could produce HA (Table III). This observation should be the result of the endogenous UDP-Glc dehydrogenase, which is responsible for producing UDP-GlcA needed for K5 capsular polysaccharide synthesis, substituting for the nonfunctional *streptococcal* enzyme. To verify this, the present inventors assayed strains with the various plasmid constructs-for UDP-Glc dehydrogenase activity (Table III). Indeed, all K5 cultures, including those with vector pAT19 alone, demonstrated this activity. SURE or χ1448 cells with plasmids encoding an intact 45-kDa protein possessed elevated enzyme activity, whereas cells with the pPDΔPstI plasmid possessed levels similar to host cells alone.

TABLE III

HA Production and UDP-Glc Dehydrogenase Activity in *E. coli* Strains Containing Various pPD41 Constructs

| STRAIN | PLASMID | HA ng/μl[b] | UDP-Glc DH pmol/min/μg[c] | PROTEIN[a] HasA | HasB |
|---|---|---|---|---|---|
| SURE |  | 0 | 3 | − | − |
|  | PD41Δ5 | 61 | 19 | + | + |
|  | PD41Δ7 | 0 | 7 | − | + |
|  | PD41ΔPstI | 0.2 | 0.8 | + | − |
|  | PD41ΔEcoRV | 0 | 14 | − | + |
| χ1448 | AT19 | 0 | 0.8 | − | − |
|  | PD41Δ5 | 21 | 17 | + | + |
|  | PD41Δ7 | 0 | 6 | − | + |
|  | PD41ΔPstI | 0.6 | 2.5 | + | − |
|  | PD41ΔEcoRV | 0 | 10 | − | + |
| K5 (Bi8337-41) | AT19 | 0 | 12 | − | − |
|  | PD41Δ5 | 253 | 12 | + | + |
|  | PD41Δ7 | 0 | 17 | − | + |
|  | PD41ΔPstI | 49 | 13 | + | − |

[a]presence or absence of intact HasA (42 kDa) or HasB (45 kDa) protein as predicted by sequence data and observed by minicell analysis.
[b]spent culture medium and SDS cell extracts were pooled and assayed; values are normalized to 1 $A_{600}$ unit of cells/ml.
[c]NADH production was measured in soluble cell extracts in the presence of UDP-Glc. There was no activity in the absence of UDP-Glc.

These above results demonstrate that the hasA gene product, HasA, is the 42-kDa protein, and the HA synthase.

The 45-kDa protein derived from hasB, is the UDP-Glc dehydrogenase (Dougherty and van de Rijn, 1993). Furthermore, studies confirm that the 42-kDa protein has both UDP-GlcNAc and UDP-GlcA glycosyl transferase activities. Crude membranes from the various constructs show HA synthase activity only in cells with the intact hasA gene. UDP-$^{14}$C-GlcA or UDP-$^{3}$H-GlcNAc are incorporated into hyaluronidase-sensitive product only in the presence of UDP-GlcNAc or UDP-GlcA, respectively. This incorporation is decreased by >98% if UDP-GalNAc or UDP-Glc are substituted for UDP-GlcNAc or if UDP-Glc or UDP-GalA are substituted for UDP-GlcA.

Dougherty and van de Rijn (Dougherty and van de Rijn, 1993) proposed in their later model that three ORFs (hasA, hasB, and hasc) are involved in HA biosynthesis. The inventors found that the S43 strain HasB is 99.8% identical at the nucleotide level to their GAS strain HasB sequence; there was perfect conservation at the protein level (not shown). The region containing the hasA and hasB genes (Dougherty and van de Rijn, 1993) possesses a restriction map consistent with the two ORFs found in pPD41Δ5 (FIG. 6). The inventors also found that a putative HasC gene is present in S43, but is not required for HA biosynthesis. Neither the HasB nor HasC proteins are needed when both sugar nucleotide precursors are present.

HA synthase possesses/significant homology with the nodC gene product of *Rhizobiumi* (DeAngelis, et al., 1994). NodC is a membrane enzyme that synthesizes chitin-li ke (poly-B-1,4-GlcNAc backbone) oligomers (Lerouge, et al., 1990) which is a very analogous activity to that of streptococcal HA synthase. NodC possesses several stretches of residues that are identical or similar to the HA synthase. Overall the two proteins are 30.6% identical. The hydropathy plots of the two proteins are very comparable, including three predicted transmembrane segments in the same location near the carboxyl terminus (DeAngelis, et al., 1994). Other proteins with homology to HA synthase include DG42 from *Xanopus laavis,* yeast chitin synthase II, and an associated protein CSH2 (Bulawa, 1992; DeAngelis, et al., 1994). The 52-kDa protein described by Prehm and coworkers (Prehm and Mausolf, 1986; Lansing, et al., 1993) is not homologous to HaSA or these other proteins. The gene cloned by these workers is not the HA synthase gene.

hasA and hasB are the only exogenous genes required to direct HA biosynthesis in most bacteria, due to the presence of one of the sugar nucleotide precursors of HA, UDP-GlcNAc, which is necessary for cell wall formation. In cells that make both UDP-GlcNAc and UDP-GlcA only HA synthase, the gene product of hasA, HasA, is needed to polymerize the HA polysaccharide (DeAngelis, et al., 1993b).

EXAMPLE V

Large Scale Production of Hyaluronic Acid

This example is directed to the engineering of a bacterium that overproduces and secretes large quantities of HA, which can then be purified from the medium. An engineered organism that overproduces HA will make it cheaper to produce larger quantities of HA than presently possible. Reduced HA production costs will increase the number and type of commercially viable products that can be developed.

The present inventors have cloned and sequenced a 3,200 base pair *Streptococcal* DNA fragment that confers on recipient bacteria the ability to make HA as described in Examples II, IV and V. Analysis of this locus revealed the presence of two tandem genes (FIG. 6). Transformation of mutant, capsule-deficient *Streptococcus* cells with these two genes restored their ability to make HA. Most importantly, putting these two genes into very different bacteria such as *Escherichia coli* or *Enterococcus faecalis* also allowed these bacteria to produce HA. This was shown visually by noting the presence of a new capsule of HA surrounding the cells (FIG. 2), and biochemically by using a specific assay to detect and quantitate HA (Tables II and III). This result indicates that after it receives the hasA and hasB genes, any type of bacteria will be able to make HA.

The nucleotide sequence of this 3.2 kb *Streptococcal* DNA fragment showed that the hasB gene encodes the enzyme UDP-glucose dehydrogenase, which is required for the cell to make UDP-glucuronic acid (UDP-GlcA), one of the two sugar precursors needed for HA biosynthesis. The second sugar precursor needed for HA synthesis is UDP-N-acetylglucosamine (UDP-GlcNAc), present in all bacteria and required for cell wall synthesis. The dehydrogenase gene was also reported by others (Dougherty and van de Rijn, 1993).

The inventors have found that any cell containing a functional UDP-Glc dehydrogenase and a functional HA synthase can make HA. Not all *E. coli* strains normally have the dehydrogenase. Those that do not will not have the UDP-GlcA needed for HA synthesis, whereas those that have the dehydrogenase (such as the K5 strain) have both sugar precursors needed for HA synthesis. When only the functional synthase was present, the K5 cells made HA, but the other strains did not (Table III). In no case did recipient bacteria make HA without a functional HA synthase gene, HasA.

To make a bacterial strain overproduce HA one may place one or more copies of both the HA synthase gene (and dehydrogenase gene if desired) into an appropriate recipient cell with functional promoters, ribosome binding sites etc. One would then find the best bacterial recipient, gene copy number and mode of gene regulation.

At each stage of development one can construct one or several bacterial strains containing the cloned HA synthase gene under the control of different regulatory elements for expression of the gene. Constructs will also be made containing combinations of the dehydrogenase and synthase genes in various copy numbers. These bacterial strains will be tested in small scale fermentation trials. One would then increase the production scale by studying fermentation cultures first on a "bench-scale" (2 liters), then "pilot" (200 liters) and finally a "commercial" scale (15,000 liters).

The strains will be assessed for their growth characteristics and their ability to produce HA. The amount, size and stability of the HA will be determined by standard testing procedures known to those of skill in the art. There is significant interest in making the highest MW HA possible, since many biomedical applications for HA require the polymer to be very long (high MW). It is likely that separate strains can be constructed to achieve production of HA of different average sizes.

Using *Bacillus subtilis* as a host cell offers distinct advantages for biotechnology and HA production. For example, the lack of endotoxin production by these cells is a big advantage in terms of FDA approval and the ease of purifying the final product (vs *Streptococcus*). The genetics of *B. subtilis* has also been extensively studied. Furthermore, these cells make both sugar precursors needed for HA synthesis (Iwasaki, et al., 1989). The inventors have observed that the plasmid pPD41Δ5 directs production of HA in *B. subtilis* strain 1A1 (with a production rate of at least 500 mg/l of a culture having an $OD_{600}$ of 1).

This recombinant construct can be grown in a very simple and inexpensive growth media, such as Spizizen's media (2 gr. $(NH_4)_2SO_4$, 14 gr. $K_2HPO_4$, 6 gr. $KH_2PO_4$, 1 gr. Sodium Citrate, and 5 gr. of glucose, per liter of water (Ausbel, et al., 1987)) supplemented with tryptophan (0.1 gr/ltr) and erythromycin (8 mg/ltr) . On the other hand, Streptococcus bacteria must be grown on a more complex media that is either expensive and/or contains large molecules that contaminate HA preparations from spent cultures. These results indicate that B. subtilis is a preferred host for the overproduction of HA. One can engineer a B. subtilis strain that produces a larger amount of HA than is produced by streptococcal strains, because the latter may possess low levels of hyaluronidase, which degrade HA.

Therefore, initial efforts are to introduce the HA synthase gene into an asporogenic strain of B. subtilis on a compatible plasmid, and also by facilitated integration using methods described by others (Smith and Youngman, 1992; Prozorov, et al., 1987; Lewandoski and Smith, 1988; Ausubel, et al., 1987). One would then isolate cells containing various copies (say 1, 3 and 5) of the synthase gene and verify that they make HA. The use of alternate promoters derived from B. subtilis can also be determined.

Based on the results of the production studies one can then modify or begin subsequent rounds of bacterial constructs. For example, one may decide to assess the effect of having different numbers of the synthase gene and only one-copy of the dehydrogenase gene. Thus, one can "fine-tune" the desired bacterial construct by successive testing and redesigning in order to optimize the quantity and quality of HA produced.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ausubel, F. M., et al. 1987. Current Prot. in Mol. Biol. Greene & Wiley-Intersci., NY.
Barson (1986), J. Pediatr. Orthop., 6:346–348.
Benjamin et al. (1976), J. Pediatr., 89:254:256.
Bitter, T. and Muir, H. (1962) Anal. Biochem. 4: 330–334.
Bulawa, C. E. (1992) Mol. Cell. Biol. 12: 1764–1776.
Caparon, M. G. and Scott, J. R. (1991) Meth. Enzymol. 204: 556–586.
Clewell, D. B., Flannagan, S. E., Ike, Y., Jones, J. M., and Gawron-Burke, C., (1988) J. Bacteriol. 170: 3046–3052.
Collins, C. H. and Lyne, P. M., (1976) Microbiological Methods, Butterworths, Boston, Mass., p.110.
Dao et al. (1985), Appl. Envir. Microbiol., 49:115–119.
DeAngelis, P. L., Papaconstantinou J., and Weigel, P. H. (1993a) J. Biol. Chem., 268:20, 14568–14571.
DeAngelis, P. L., Papaconstantinou J., and Weigel, P. H. (1993b) J. Biol. Chem., 268:26, 19181–19184.
DeAngelis, P. L., Yang, N., and Weigel, P. H. (1994) Biochemical and Biophysical Research Communications, Vol. 199, No. 1, pp. 1–20 (Feb. 28, 1994).
Dinn (1971), J. Ir. Med. Assoc., 64:50–51.
Dochez, A. R., Avery, O. T., and Lancefield, R. C. (1919) J. Exp. Med. 30: 179–213.
Dougherty, B. A. and van de Rijn, I. (1992) J. Exp. Med. 175: 1291–1299.
Dougherty, B. A. and van de Rijn, I. (1993) J. Biol. Chem. 268:7118–7124.
Dunny, G. M., Lee, L. N. and LeBlanc, D. J. (1991) Appl. Environ. Microbiol. 57: 1194–1201.
DuPont Biotech. Update, 4, #4, July 1989.
Ehtesham, N. Z. and Hasnain, S. E. (1991) BioTechniques 11: 718–721.
European Patent Application EP144019.
European Patent Application EP266578.
European Patent Application EP244757.
Evered, D. and Whelan, J. (eds.) 1989. The Biology of Hyaluronan. Wiley, Chichester, U.K.
Fiers et al., Nature, 273:113 (1978).
Gawron-Burke, C. and Clewell, D. B. (1984) J. Bacteriol. 159: 214–221.
Gren, E. J. (1984) Biochimie 66:1–29.
Guerrero, R., Pedros-Alio, C., Schmidt, T. M., and Mas, J. (1985), Microbiologia, 1:53–65.
Gupta, D. S. Jann, B., Schmidt, G., Golecki, J. R., Orskov, I., Orskov, F., and Jann, K., (1982) FEMS Microbiol. Letters 14:75–78.
Håkansson S., and Holm S. E., (1986) Acta Path. Microbiol. Immunol. Scand. Sect. B 94:139–43.
Hirsch et al. (1960), J. Exp. Med., 111:309–322.
Ishimoto et al. (1967), Biochim. Biophys. Acta, 148:296–297.
Iwasaki, H., Araki, Y., Kaya, S. and Ito, E. (1989) Eur. J. Biochem. 178:635–641.
Jones, Genetics, 85:12 (1977).
Kass et al. (1944), J. Exp. Med., 79:319–330.
Kendall, F., Heidelberger, M., and Dawson, M. (1937) J. Biol. Chem. 118: 61–69.
Kyte & Doolittle (1982) J. Mol. Biol. 157:105–132
Laemmli, U.K. (1970) Nature 227: 680–685.
Lansing, M., Lellig, S., Mausolf, A., Martini, I., Crescenzi, F., O'Regan, M., and Prehm, P. (1993) Biochem. J. 289: 179–184.
Laurent, T. C. and Fraser, J. R. E. (1992) FASEB J. 6: 2397–2404.
Lerouge, P., Roche, P., Faucher, C., Maillet, F., Truchet, G., Prome, J. C., and Denarie, J. (1990) Nature 344: 781–784.
Lewandoski, M. and Smith, I. (1988) Plasmid 20:148–154.
MacLennan, A. P. 1956. J. Gen. Microbiol. 14:134–142.
Markovitz, A., Cifonelli, J. A., and Dorfman, A. (1959) J. Biol. Chem. 234: 2343–2350.
Markovitz et al. (1962), J. Biol. Chem., 237:273–279.
Matsumura, P., Silverman, M. and Simon, M. (1977) J. Bacteriol. 132: 996–1002.
Maxam et al. (1980), Meth. Enzymol., 65:499.
Meagher, R. B., Tait, R. C., Betlach, M. and Boyer, H. W. (1977) Cell 10: 521–536.
Messing et al. (1981), Nucl. Acids Res., 9:309.
Min, H. and Cowman, M. K. (1986) Anal. Biochem. 155: 275–285.

Ng, K. F. and Schwartz, N. B. (1989) J. Biol. Chem. 264: 11776–11783.

O'Connor, S. P. and Cleary, P. P. (1987) J. Infect. Dis. 156: 495–504.

Prehm, P. (1983) Biochem. J. 211: 181–189.

Prehm, P. and Mausolf, A. 1986. Biochem. J. 235:887–889.

Prozorov, A. A., Poluektova, E. U., Savchenko, G. V., Nezmetdinova, V. Z. and Khasanov, F. K. (1987) Gene 57: 221–227.

Quinn, A. W. and Singh, K. P., (1957) Biochem. J. 95:290–201.

Rizkallah et al. (1988), J. Infect. Dis., 158:1092–1094.

Rotta (1988), APMIS Suppl., 3:3–7.

Sambrook, J., Fritsch, E. F., and Maniatis, T., (1989) *Molecular Cloning: A Laboratory Manual.* 2nd Ed., Cold Spring Harbor Laboratory, Cold Spring Harbor, N.Y.

Sanger et al. (1977), Proc. Natl. Acad. Sci. USA, 74:5463–5467.

Schaechter, M., Medoff, G., and Schlessinger, D., editors, (1989) *Mechanisms of Microbial Disease,* Williams and Wilkins, Baltimore, Md.

Scott et al. (1964), Histochemie, 4:73–85.

Siefkin et al. (1983), J. Clin. Microbiol., 17:386–388.

Smith, K. and Youngman, P. (1992) Biochimie 74: 705–711.

Stoolmiller et al. (1969), J. Biol. Chem., 244:236–246.

Studier et al. (1990), Meth. Enzymol. 185:60–89

Sugahara et al. (1979), J. Biol. Chem., 254:6252–6261.

Tengblad, A. (1980) Biochem. J. 185:101–105.

Tissue Culture, Academic Press, Kruse and Patterson, editors (1973).

Trieu-Cuot, P., Carlier, C., Poyart-Salmeron, C. and Courvalin, P. (1991) Gene 102:99–104.

Triscott, M. X. and van de Rijn, I. (1986) J. Biol. Chem. 261: 6004–6009.

van de Rijn, I. and Drake, R. R. (1992) J. Biol. Chem. 267: 24302–24306.

Wessels, M. R., Moses, A. E., Goldberg, J. B., and DiCesare, T. J., (1991) Proc. Natl. Acad. Sci. USA, 88:8317–8321.

Whitnack et al. (1981), Infect. Immun., 31:985–991.

---

What is claimed is:

1. A method of detecting a DNA species comprising the steps of:
   (a) obtaining a DNA sample;
   (b) contacting said DNA sample with a nucleic acid segment in accordance with SEQ ID NO:1 under conditions effective to allow hybridization to form a complex; and
   (c) detecting said complex.

2. A method for detecting a bacterial cell that expresses hyaluronic acid synthase, comprising the steps of:
   (a) obtaining a bacterial cell sample suspected of expressing hyaluronan synthase;
   (b) contacting nucleic acids from said cell sample with a nucleic acid segment in accordance with SEQ ID NO:1 under conditions effective to allow hybridization of substantially complementary nucleic acid sequences; and
   (c) identifying the presence of hybridized complexes containing substantially complementary nucleic acid sequences within said sample; wherein the presence of increased levels of said substantially complementary nucleic acid sequence is indicative of a bacterial strain that expresses hyaluronan synthase.

3. The method of claim 1, wherein the nucleic acids contacted are located within said cell.

4. The method of claim 1, wherein the nucleic acids are separated from said cell prior to contact.

5. The method of claim 1, wherein the nucleic acid segment comprises a detectable label and hybridized complexes are detected by detecting said label.

6. The method of claim 2, wherein said nucleic acid segment comprises a radio-, an enzymatic-, a fluorescent-, a biotinyl-, or a chemiluminescent-label.

* * * * *

UNITED STATES PATENT AND TRADEMARK OFFICE
CERTIFICATE OF CORRECTION

PATENT NO. : 6,855,502 B2
DATED : February 15, 2005
INVENTOR(S) : Paul Weigel et al.

It is certified that error appears in the above-identified patent and that said Letters Patent is hereby corrected as shown below:

Column 3,
Line 58, after "acid" and before "and" add -- (GlaVa) --.
Line 59, after "N-acetylglucosamine" and before "sugars" add -- (GlaVa) --.

Column 5,
Line 21, after "of" and before "skill" add -- ordinary --; and after "skill" and before "will" add -- in the art --.

Column 6,
Line 12, after "present" delete "intention" and replace with -- invention --.

Column 7,
Line 15, delete "oligonueleotides" and replace with -- oligonucleotides --.

Column 13,
Line 58, delete "phil0" and replace with -- Φ10 --.

Column 18,
Line 19, delete "which" and replace with -- Which --.

Column 19,
Line 21, delete "zooepidemlcus" and replace with -- zooepidemicus --.

Signed and Sealed this

Twentieth Day of December, 2005

JON W. DUDAS
*Director of the United States Patent and Trademark Office*

UNITED STATES PATENT AND TRADEMARK OFFICE
CERTIFICATE OF CORRECTION

PATENT NO. : 6,855,502 B2
APPLICATION NO. : 10/124222
DATED : February 15, 2005
INVENTOR(S) : Paul H. Weigel, Paul L. DeAngelis and John Papaconstantinou It is certified that error appears in the above-identified patent and that said Letters Patent is hereby corrected as shown below:

Column 1, lines 14-16: Delete entirety of paragraph and replace with -- This invention was made with government support under Contract Number GM035978 awarded by the National Institutes of Health. The government has certain rights in the invention. --

Signed and Sealed this

Fifth Day of October, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 1512
<212> TYPE: DNA
<213> ORGANISM: Streptococcus pyogenes
<220> FEATURE:
<221> NAME/KEY: CDS
<222> LOCATION: (193)..(1449)
<223> OTHER INFORMATION:
<220> FEATURE:
<221> NAME/KEY: CDS
<222> LOCATION: (1488)..(1508)
<223> OTHER INFORMATION:

<400> SEQUENCE: 1
aattattttg ggataatttta tttaatatat attaaataaa ttatcctgat ttttcttttt      60 cggggaatt tttttaatgg aaacacaatt ttattaaaaa tatctctata tctagttgac     120
attatttctt atttatatta taatattgag gtcctttctt tcaaggaaat taaaaaagaa     180
agaggtgtaa tt gtg cct att ttt aaa aaa act tta att gtt tta tcc ttt     231
           Val Pro Ile Phe Lys Lys Thr Leu Ile Val Leu Ser Phe
            1               5                  10 att ttt ttg ata tct atc ttg att tat cta aat atg tat cta ttt gga     279
Ile Phe Leu Ile Ser Ile Leu Ile Tyr Leu Asn Met Tyr Leu Phe Gly
     15                  20                  25 aca tca act gta gga att tat gga gta ata tta ata acc tat cta gtt     327
Thr Ser Thr Val Gly Ile Tyr Gly Val Ile Leu Ile Thr Tyr Leu Val
 30                  35                  40                  45 atc aaa ctt gga tta tct ttc ctt tat gag cca ttt aaa gga aat cca     375
Ile Lys Leu Gly Leu Ser Phe Leu Tyr Glu Pro Phe Lys Gly Asn Pro
                 50                  55                  60 cat gac tat aaa gtt gct gct gta att cct tct tat aat gaa gat gcc     423
His Asp Tyr Lys Val Ala Ala Val Ile Pro Ser Tyr Asn Glu Asp Ala
             65                  70                  75 gag tca tta tta gaa aca ctt aaa agt gtg tta gca cag acc tat ccg     471
Glu Ser Leu Leu Glu Thr Leu Lys Ser Val Leu Ala Gln Thr Tyr Pro
         80                  85                  90 tta tca gaa att tat att gtt gat gat ggg agt tca aac aca gat gca     519
Leu Ser Glu Ile Tyr Ile Val Asp Asp Gly Ser Ser Asn Thr Asp Ala
```

-continued

| | | | | | | | | | | | | | | | | |
|---|---|---|---|---|---|---|---|---|---|---|---|---|---|---|---|---|
| | | | | 95 | | | | | 100 | | | | | 105 | | |
| ata | caa | tta | att | gaa | gag | tat | gta | aat | aga | gaa | gtg | gat | att | tgt | cga | 567 |
| Ile | Gln | Leu | Ile | Glu | Glu | Tyr | Val | Asn | Arg | Glu | Val | Asp | Ile | Cys | Arg | |
| 110 | | | | | 115 | | | | | 120 | | | | | 125 | |
| aac | gtt | atc | gtt | cac | cgt | tcc | ctt | gtc | aat | aaa | gga | aaa | cgc | cat | gct | 615 |
| Asn | Val | Ile | Val | His | Arg | Ser | Leu | Val | Asn | Lys | Gly | Lys | Arg | His | Ala | |
| | | | | 130 | | | | | 135 | | | | | 140 | | |
| caa | gcg | tgg | gca | ttt | gaa | aga | tct | gac | gct | gac | gtt | ttt | tta | acc | gta | 663 |
| Gln | Ala | Trp | Ala | Phe | Glu | Arg | Ser | Asp | Ala | Asp | Val | Phe | Leu | Thr | Val | |
| | | | 145 | | | | | 150 | | | | | 155 | | | |
| gac | tca | gat | act | tat | atc | tat | cca | aat | gcc | tta | gaa | gaa | ctc | cta | aaa | 711 |
| Asp | Ser | Asp | Thr | Tyr | Ile | Tyr | Pro | Asn | Ala | Leu | Glu | Glu | Leu | Leu | Lys | |
| | | 160 | | | | | 165 | | | | | 170 | | | | |
| agc | ttc | aat | gat | gag | aca | gtt | tat | gct | gca | aca | gga | cat | ttg | aat | gct | 759 |
| Ser | Phe | Asn | Asp | Glu | Thr | Val | Tyr | Ala | Ala | Thr | Gly | His | Leu | Asn | Ala | |
| | 175 | | | | | 180 | | | | | 185 | | | | | |
| aga | aac | aga | caa | act | aat | cta | tta | acg | cga | ctt | aca | gat | atc | cgt | tac | 807 |
| Arg | Asn | Arg | Gln | Thr | Asn | Leu | Leu | Thr | Arg | Leu | Thr | Asp | Ile | Arg | Tyr | |
| 190 | | | | | 195 | | | | | 200 | | | | | 205 | |
| gat | aat | gcc | ttt | ggg | gtg | gag | cgt | gct | gct | caa | tca | tta | aca | ggt | aat | 855 |
| Asp | Asn | Ala | Phe | Gly | Val | Glu | Arg | Ala | Ala | Gln | Ser | Leu | Thr | Gly | Asn | |
| | | | | 210 | | | | | 215 | | | | | 220 | | |
| att | tta | gtt | tgc | tca | gga | cca | ttg | agt | att | tat | cga | cgt | gaa | gtg | att | 903 |
| Ile | Leu | Val | Cys | Ser | Gly | Pro | Leu | Ser | Ile | Tyr | Arg | Arg | Glu | Val | Ile | |
| | | | 225 | | | | | 230 | | | | | 235 | | | |
| att | cct | aac | tta | gag | cgc | tat | aaa | aat | caa | aca | ttc | cta | ggt | tta | cct | 951 |
| Ile | Pro | Asn | Leu | Glu | Arg | Tyr | Lys | Asn | Gln | Thr | Phe | Leu | Gly | Leu | Pro | |
| | | 240 | | | | | 245 | | | | | 250 | | | | |
| gtt | agc | att | ggg | gat | gat | cga | tgt | tta | aca | aat | tat | gct | att | gat | tta | 999 |
| Val | Ser | Ile | Gly | Asp | Asp | Arg | Cys | Leu | Thr | Asn | Tyr | Ala | Ile | Asp | Leu | |
| | 255 | | | | | 260 | | | | | 265 | | | | | |
| gga | cgc | act | gtc | tac | caa | tca | aca | gct | aga | tgt | gat | act | gat | gta | cct | 1047 |
| Gly | Arg | Thr | Val | Tyr | Gln | Ser | Thr | Ala | Arg | Cys | Asp | Thr | Asp | Val | Pro | |
| 270 | | | | | 275 | | | | | 280 | | | | | 285 | |
| ttc | caa | tta | aaa | agt | tat | tta | aag | caa | caa | aat | cga | tgg | aat | aaa | tct | 1095 |
| Phe | Gln | Leu | Lys | Ser | Tyr | Leu | Lys | Gln | Gln | Asn | Arg | Trp | Asn | Lys | Ser | |
| | | | | 290 | | | | | 295 | | | | | 300 | | |
| ttt | ttt | aga | gaa | tct | att | att | tct | gtt | aaa | aaa | att | ctt | tct | aat | ccc | 1143 |
| Phe | Phe | Arg | Glu | Ser | Ile | Ile | Ser | Val | Lys | Lys | Ile | Leu | Ser | Asn | Pro | |
| | | | 305 | | | | | 310 | | | | | 315 | | | |
| atc | gtt | gcc | tta | tgg | act | att | ttc | gaa | gtc | gtt | atg | ttt | atg | atg | ttg | 1191 |
| Ile | Val | Ala | Leu | Trp | Thr | Ile | Phe | Glu | Val | Val | Met | Phe | Met | Met | Leu | |
| | | 320 | | | | | 325 | | | | | 330 | | | | |
| att | gtc | gca | att | ggg | aat | ctt | ttg | ttt | aat | caa | gct | att | caa | tta | gac | 1239 |
| Ile | Val | Ala | Ile | Gly | Asn | Leu | Leu | Phe | Asn | Gln | Ala | Ile | Gln | Leu | Asp | |
| | 335 | | | | | 340 | | | | | 345 | | | | | |
| ctt | att | aaa | ctt | ttt | gcc | ttt | tta | tcc | atc | atc | ttt | atc | gtt | gct | tta | 1287 |
| Leu | Ile | Lys | Leu | Phe | Ala | Phe | Leu | Ser | Ile | Ile | Phe | Ile | Val | Ala | Leu | |
| 350 | | | | | 355 | | | | | 360 | | | | | 365 | |
| tgt | cgt | aat | gtt | cat | tat | atg | gtc | aaa | cat | cct | gct | agt | ttt | ttg | tta | 1335 |
| Cys | Arg | Asn | Val | His | Tyr | Met | Val | Lys | His | Pro | Ala | Ser | Phe | Leu | Leu | |
| | | | | 370 | | | | | 375 | | | | | 380 | | |
| tct | cct | ctg | tat | gga | ata | tta | cac | ttg | ttt | gtc | tta | cag | ccc | cta | aaa | 1383 |
| Ser | Pro | Leu | Tyr | Gly | Ile | Leu | His | Leu | Phe | Val | Leu | Gln | Pro | Leu | Lys | |
| | | | 385 | | | | | 390 | | | | | 395 | | | |
| ctt | tat | tct | tta | tgc | acc | att | aaa | aat | acg | gaa | tgg | gga | aca | cgt | aaa | 1431 |
| Leu | Tyr | Ser | Leu | Cys | Thr | Ile | Lys | Asn | Thr | Glu | Trp | Gly | Thr | Arg | Lys | |
| | | 400 | | | | | 405 | | | | | 410 | | | | |
| aag | gtc | act | att | ttt | aaa | taatatatgc | atcgagtagt | tagagaagga | gtaatttt | | | | | | | 1487 |

```
Lys Val Thr Ile Phe Lys
    415 atg aaa ata gca gtt gct gga tcag                                    1512
Met Lys Ile Ala Val Ala Gly
420             425
```

<210> SEQ ID NO 2
<211> LENGTH: 419
<212> TYPE: PRT
<213> ORGANISM: Streptococcus pyogenes

<400> SEQUENCE: 2

```
Val Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
        50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
```

-continued

```
                340                 345                 350
Leu Phe Ala Phe Leu Ser Ile Ile Phe Ile Val Ala Leu Cys Arg Asn
                355                 360                 365

Val His Tyr Met Val Lys His Pro Ala Ser Phe Leu Leu Ser Pro Leu
            370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 3
<211> LENGTH: 7
<212> TYPE: PRT
<213> ORGANISM: Streptococcus pyogenes

<400> SEQUENCE: 3

Met Lys Ile Ala Val Ala Gly
1               5

<210> SEQ ID NO 4
<211> LENGTH: 419
<212> TYPE: PRT
<213> ORGANISM: Streptococcus pyogenes

<400> SEQUENCE: 4

Val Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240
```

-continued

```
Leu Glu Arg Tyr Lys Asn Gln Thr Phe Leu Gly Leu Pro Val Ser Ile
            245                 250                 255
Gly Asp Asp Arg Cys Leu Thr Asn Tyr Ala Ile Asp Leu Gly Arg Thr
        260                 265                 270
Val Tyr Gln Ser Thr Ala Arg Cys Asp Thr Asp Val Pro Phe Gln Leu
    275                 280                 285
Lys Ser Tyr Leu Lys Gln Gln Asn Arg Trp Asn Lys Ser Phe Phe Arg
290                 295                 300
Glu Ser Ile Ile Ser Val Lys Lys Ile Leu Ser Asn Pro Ile Val Ala
305                 310                 315                 320
Leu Gln Thr Ile Phe Glu Val Val Met Phe Met Leu Ile Val Ala
                325                 330                 335
Ile Gly Asn Leu Leu Phe Asn Gln Ala Ile Gln Leu Asp Leu Ile Lys
                340                 345                 350
Leu Phe Ala Phe Leu Ser Ile Ile Phe Ile Val Ala Leu Cys Arg Asn
            355                 360                 365
Val His Tyr Met Val Lys His Pro Ala Ser Phe Leu Leu Ser Pro Leu
    370                 375                 380
Tyr Gly Ile Leu His Leu Phe Val Leu Gln Pro Leu Lys Leu Tyr Ser
385                 390                 395                 400
Leu Cys Thr Ile Lys Asn Thr Glu Trp Gly Thr Arg Lys Lys Val Thr
                405                 410                 415
Ile Phe Lys
```

<210> SEQ ID NO 5
<211> LENGTH: 7
<212> TYPE: PRT
<213> ORGANISM: Streptococcus pyogenes

<400> SEQUENCE: 5

```
Met Lys Ile Ala Val Ala Gly
1               5
```

<210> SEQ ID NO 6
<211> LENGTH: 16
<212> TYPE: DNA
<213> ORGANISM: ARTIFICIAL SEQUENCE
<220> FEATURE:
<223> OTHER INFORMATION: OLIGONUCLEOTIDE PROBE

<400> SEQUENCE: 6
aaagtgtgat aagtcc                                                 16

<210> SEQ ID NO 7
<211> LENGTH: 19
<212> TYPE: DNA
<213> ORGANISM: ARTIFICIAL SEQUENCE
<220> FEATURE:
<223> OTHER INFORMATION: OLIGONUCLEOTIDE PROBE

<400> SEQUENCE: 7
tggcacaata tgtcagccc                                              19

<210> SEQ ID NO 8
<211> LENGTH: 19
<212> TYPE: DNA
<213> ORGANISM: ARTIFICIAL SEQUENCE
<220> FEATURE:
<223> OTHER INFORMATION: OLIGONUCLEOTIDE PROBE

```
<400> SEQUENCE: 8
tatggcttag tgccattcg                                                19

<210> SEQ ID NO 9
<211> LENGTH: 19
<212> TYPE: DNA
<213> ORGANISM: ARTIFICIAL SEQUENCE
<220> FEATURE:
<223> OTHER INFORMATION: OLIGONUCLEOTIDE PROBE

<400> SEQUENCE: 9
caatcatacc accaactgc                                                19
```